US010300085B2

(12) United States Patent
Shimamoto et al.

(10) Patent No.: US 10,300,085 B2
(45) Date of Patent: May 28, 2019

(54) NUTRITIONAL COMPOSITION

(71) Applicant: DAICEL CORPORATION, Osaka-shi, Osaka (JP)

(72) Inventors: Shu Shimamoto, Tokyo (JP); Toshikazu Nakamura, Himeji (JP); Shizuka Ukita, Himeji (JP); Tsuyoshi Nakamura, Fukuoka (JP); Ryoko Yamauchi, Fukuoka (JP); Hiroshi Kobayashi, Fukuoka (JP); Tatsuya Morita, Shizuoka (JP); Tomomi Genda, Shizuoka (JP)

(73) Assignee: DAICEL CORPORATION, Osaka-Shi, Osaka (JP)

( * ) Notice: Subject to any disclaimer, the term of this patent is extended or adjusted under 35 U.S.C. 154(b) by 60 days.

(21) Appl. No.: 15/128,682

(22) PCT Filed: Mar. 20, 2015

(86) PCT No.: PCT/JP2015/058579
§ 371 (c)(1),
(2) Date: Sep. 23, 2016

(87) PCT Pub. No.: WO2015/146853
PCT Pub. Date: Oct. 1, 2015

(65) Prior Publication Data
US 2017/0100426 A1    Apr. 13, 2017

(30) Foreign Application Priority Data
Mar. 24, 2014   (WO) .................. PCT/JP2014/058069

(51) Int. Cl.
*A61K 31/717*  (2006.01)
*A23L 33/24*   (2016.01)

(52) U.S. Cl.
CPC ............ *A61K 31/717* (2013.01); *A23L 33/24* (2016.08)

(58) Field of Classification Search
CPC .... A61K 31/717; A23K 20/163; A23K 50/75; A23K 50/40; A23L 33/24; A23V 2002/00
USPC ......................................... 514/57; 424/93.41
See application file for complete search history.

(56) References Cited

U.S. PATENT DOCUMENTS

| | | | |
|---|---|---|---|
| 5,142,034 A | 8/1992 | Bellas et al. | |
| 5,914,397 A | 6/1999 | Kiyose et al. | |
| 2002/0098112 A1 | 7/2002 | Hayashi | |
| 2002/0183764 A1 | 12/2002 | Kinugasa et al. | |
| 2004/0024198 A1 | 2/2004 | Shibata et al. | |
| 2008/0176819 A1* | 7/2008 | Lynch ................. | A61K 31/717 514/57 |
| 2008/0194807 A1 | 8/2008 | Buchanan et al. | |
| 2009/0093441 A1* | 4/2009 | Lynch ................. | A61K 31/717 514/57 |
| 2009/0171079 A1 | 7/2009 | Higuchi | |
| 2010/0074951 A1 | 3/2010 | Kim et al. | |
| 2011/0166340 A1 | 6/2011 | Shibata et al. | |
| 2016/0032020 A1 | 2/2016 | Ukita et al. | |
| 2016/0317568 A1 | 11/2016 | Shimamoto et al. | |

FOREIGN PATENT DOCUMENTS

| | | |
|---|---|---|
| EP | 0 822 201 A2 | 2/1998 |
| EP | 1 205 183 A2 | 5/2002 |
| EP | 2 075 261 A1 | 7/2009 |
| JP | 58-34801 A | 3/1983 |
| JP | 62-7701 A | 1/1987 |
| JP | 9-77801 A | 3/1997 |
| JP | 2883911 B2 | 2/1999 |
| JP | 2003-201301 A | 7/2003 |
| JP | 2009-155555 A | 7/2009 |
| JP | 2010-508267 A | 3/2010 |
| JP | 2010-100583 A | 5/2010 |
| JP | 5921762 B2 | 5/2016 |
| WO | WO 91/16358 A1 | 10/1991 |
| WO | WO 02/30485 A1 | 4/2002 |
| WO | WO 2005/054297 A2 | 6/2005 |
| WO | WO 2014/142166 A1 | 9/2014 |
| WO | WO 2015/093067 A1 | 6/2015 |

OTHER PUBLICATIONS

Glossary of medical education terms, Institute of International Medical Education. http://www.iime.org/glossary.htm Accessed in Mar. 2013. (Year: 2013).*

(Continued)

*Primary Examiner* — Yih-Horng Shiao
(74) *Attorney, Agent, or Firm* — Birch, Stewart, Kolasch & Birch, LLP

(57) ABSTRACT

A nutrient composition, a lipid metabolism-improving agent, and prophylactic and/or therapeutic agents typically for inflammatory bowel diseases, immune disorders, cancers, non-alcoholic steatohepatitis, obesity, diabetes, and hypercholesterolemia each contain a cellulose acetate having a total degree of acetyl substitution of 0.4 to 1.1. The cellulose acetate may be one having a compositional distribution index (CDI) of 2.0 or less, where the CDI is defined by the formula:

CDI=(Measured value of half height width of chemical composition)/(Theoretical value of half height width of chemical composition)

where the measured value of half height width of chemical composition represents a half height width of chemical composition determined by HPLC analysis of a cellulose acetate propionate prepared by propionylating all residual hydroxy groups of the cellulose acetate (sample), and the theoretical value of half height width of chemical composition =2.35482
$\sqrt{3*DPw*(DS/3)*(1-DS/3)}/DPw$     [Math. 1]

where DS is the total degree of acetyl substitution; and DPw is a weight-average degree of polymerization determined by a GPC-light scattering method using a cellulose acetate propionate prepared by propionylating all residual hydroxy groups of the cellulose acetate (sample).

9 Claims, 11 Drawing Sheets

(56) References Cited

OTHER PUBLICATIONS

Anderson et al. Health benefits of dietary fiber. Nutrition Reviews 67(4):188-205, 2009. (Year: 2009).*
Extended European Search Report dated Nov. 7, 2017, in European Patent Application No. 15770345.5.
Wheatley, T. A., "Water Soluble Cellulose Acetate: A Versatile Polymer for Film Coating," Drug Development and Industrial Pharmacy (2007), vol. 33, pp. 281-290.
International Search Report for PCT/JP2015/058579 (PCT/ISA/210) dated Apr. 28, 2015.
Kishimoto et al., "Effects of Long-term Administration of Indigestible Dextrin on Visceral Fat Accumulation", J. Jpn. Assoc. Dietary Fiber Res., vol. 4, No. 2, 2000, pp. 59-65.
Thomas, et al. "Subchronic oral toxicity of cellulose acetate in rats", Food and Chemical Toxicology, vol. 29, No. 7, 1991, pp. 453-458.
Written Opinion of the International Searching Authority for PCT/JP2015/058579 (PCT/ISA/237) dated Apr. 28, 2015.
Japanese Office Action, dated Jun. 20, 2017, for Japanese Application No. 2016-079434, with an English machine translation.
Extended European Search Report dated Jul. 28, 2017, in European Patent Application No. 14873093.0.
Atarashi et al., "Induction of Colonic Regulatory T Cells by Indigenous *Colstridium* Species," Science (Jan. 21, 2011), vol. 331, pp. 337-341, with supporting online material.
Notification of Reasons for Refusal dated Mar. 21, 2017, in Japanese Patent Application No. 2015-503703, with English translation.
Ferguson et al., "Production of short-chain fatty acids following in vitro fermentation of saccharides, saccharide esters, fructo-oligosaccharides, starches . . . " J. Sci. Food Agric., vol. 80, 2000, pp. 166-170.
U.S. Office Action for U.S. Appl. No. 15/106,095, dated Feb. 22, 2018.

* cited by examiner

MEAN ±SEM (g), NA, NHF: n = 7, SHF: n = 6, SHF+W: n = 5, (p < 0.05)

MEAN ±SEM, (P < 0.05)

NUTRITIONAL COMPOSITION

TECHNICAL FIELD

The present invention relates to a nutrient composition (nutritional composition) having lipid metabolism-improving action. The nutrient composition highly effectively contributes to decrease of neutral lipids (triglycerides). The nutrient composition is expected to offer prophylactic and/or therapeutic effects typically on obesity, diabetes, and hyperlipidemia. The present invention also relates to a lipid metabolism-improving agent and to a prophylactic and/or therapeutic agent for inflammatory bowel diseases and/or immune disorder (such as allergic diseases). In addition, the present invention also relates to a prophylactic and/or therapeutic agent for cancer, to a prophylactic and/or therapeutic agent for non-alcoholic steatohepatitis, and to a prophylactic and/or therapeutic agent for hypercholesterolemia. This application claims priority to International Application Number PCT/JP2014/058069 filed to Japan Mar. 24, 2014, the entire contents of which are incorporated herein by reference.

BACKGROUND ART

With improving dietary habit and increasing Western diet, high-calorie, high-fat diets are ingested at increasing opportunities. Excessive lipid/fat ingestion causes obesity and serum lipid level elevation, and this increases the risk of onset of complications associated therewith.

Some substances are undegradable in the body and are therefore considered to prevent diabetes by restraining blood glucose level elevation and to be effective for dieting by restraining fat absorption. Indigestible dextrin (resistant dextrin) has been known as one of these substances (see Non Patent Literature (NPL) 1). Patent Literature (PTL) 1 proposes a lipid metabolism-improving agent containing a branched α-glucan having a specific structure. This agent is proposed as a lipid metabolism-improving agent containing dietary fibers that are safe even when ingested for a long time.

Advantageously, the indigestible dextrin does not impede mineral absorption and is approximately free of adverse effects. However, the indigestible dextrin has room for the further improvements in triglyceride decrease. In addition, the indigestible dextrin may cause diarrhea when ingested in a large amount.

Independently, soluble dietary fibers such as carboxymethylcellulose (CMC), indigestible dextrin, pectin, and polydextroses are used as food additives. These soluble dietary fibers are considered to have functions (i) to (iii) as follows. (i) The soluble dietary fibers increase the viscosity of intestinal contents and retard sugar absorption to thereby restrain postprandial abrupt elevation of blood glucose levels. (ii) The soluble dietary fibers adsorb bile acids and cholesterols and excrete them from the body to thereby restrain serum cholesterol level elevation. (iii) The soluble dietary fibers are fermented/decomposed in the intestinal tract to increase the amount of short-chain fatty acids to thereby promote the development or growth of the intestinal epithelial cells. However, increase of intestinal bacterial groups including short-chain fatty acid-producing bacteria has not yet been investigated, except the increase typically in the case of fermented lactic-drinks.

CITATION LIST

Patent Literature

PTL 1: Japanese Unexamined Patent Application Publication No. 2010-100583

Non Patent Literature

NPL 1: Journal of Japanese Association for Dietary Fiber Research, Vol. 4 (2000), No. 2, pp. 59-65

SUMMARY OF INVENTION

Technical Problem

The present invention has an object to provide a nutrient composition and a livestock feed, both of which highly effectively contribute to triglyceride decrease, are still intestine friendly, and are highly safe.

The present invention has another object to provide a lipid metabolism-improving agent that is intestine friendly and is highly safe.

The present invention has still another object to provide a prophylactic and/or therapeutic agent for inflammatory bowel diseases and/or immune disorder, where the agent is intestine friendly and is highly safe.

The present invention has yet another object to provide novel prophylactic and/or therapeutic agent for cancer.

The present invention has another object to provide a prophylactic and/or therapeutic agent for non-alcoholic steatohepatitis.

The present invention has another object to provide a prophylactic and/or therapeutic agent typically for obesity and/or diabetes.

The present invention has another object to provide a prophylactic and/or therapeutic agent for hypercholesterolemia.

Solution to Problem

After intensive investigations to achieve the objects, the inventors of the present invention have found that a cellulose acetate with a low degree of substitution (cellulose acetate with a low degree of substitution) highly effectively contributes to decreased blood triglyceride levels (blood neutral lipid levels) and that the cellulose acetate with a low degree of substitution has the function of increasing an OTU group (OTU 940) including *Clostridium* subcluster XIVa, which subcluster is beneficial in the intestinal flora. The *Clostridium* subcluster XIVa is expected to have therapeutic and prophylactic effects on inflammatory bowel diseases (such as Crohn disease and ulcerative colitis listed by the Ministry of Health, Labour and Welfare (Japan)) and immune disorder such as allergosis, which are intractable diseases. Thus, the ingestion and/or administration of the cellulose acetate with a low degree of substitution is highly expected to improve the intestinal flora and to offer therapeutic and prophylactic effects on the inflammatory bowel diseases and immune disorder such as allergosis.

The inventors have also found that the cellulose acetate with a low degree of substitution has the function of decreasing OTU 919 and OTU 338 including *Clostridium* cluster XI in the intestinal flora. The *Clostridium* cluster XI produces secondary bile acids that are suspected to be involved in carcinogenesis in the liver. Accordingly, the ingestion or administration of the cellulose acetate with a low degree of substitution decreases this bacterial group to improve the intestinal flora, and is highly expected to have prophylactic and/or therapeutic effects on liver cancer.

In addition, the inventors have found that the cellulose acetate with a low degree of substitution has the function of significantly increasing *Bacteroides xylanisolvens* and *Bacteroides ovatus* in the intestinal flora.

Thomsen-Friedenreich antigen α (TFα) is a carbohydrate antigen that is specifically expressed on cancer cell surface and is a promising target for cancer therapy. The immunity (anti-TFα antibody) for TFα is often also found in healthy human sera and is considered to play a key role in immune surveillance in cancer (e.g., Springer, Journal of Molecular Medicine, 75, pp. 594-602, 1997; and Kurtenkov et al., Acta Oncologica, 46, pp. 316-323, 2007). A proposed reason why healthy humans not having TFα-expressing cancer cells can previously have the anti-TFα antibody is that *Bacteroides ovatus*, one of intestinal bacteria (enteric bacteria), expresses a TFα structure; and on the basis of this, the microorganism, when used, may possibly provide anticancer vaccines (Henderson et al., Glycobiology, 21 (10), p. 1277, 2011). In addition, it has been reported that *Bacteroides xylanisolvens* expresses TFα having higher antigenicity and is useful as a therapeutic agent for cancers (US 2014/0302093 A1).

Consequently, the cellulose acetate with a low degree of substitution, which significantly increases *Bacteroides xylanisolvens* and *Bacteroides ovatus* in the intestines when ingested or administered, is expected to allow the subject to acquire the immunity against TFα and to thereby offer therapeutic and prophylactic effects on cancers that express TFα.

Further, the inventors have found that the cellulose acetate with a low degree of substitution, when ingested or administered, also increases *Akkermansia muciniphila* in the intestinal flora.

*Akkermansia muciniphila* has been reported to offer restraining actions on obesity and type II diabetes in animal trials (Everard et al., Proceedings of the National Academy of Sciences, 110(22), p. 9066, 2013; Lukovac et al., mBio, 5(4):e01438-14. doi:10.1128/mBio.01438-14, 2014; and Everard et al., Diabetes, 60, p. 2775, 2011). Thus, the cellulose acetate with a low degree of substitution, when ingested or administered, is expected to offer therapeutic and prophylactic effects typically on obesity and type II diabetes.

The inventors have also found that the cellulose acetate with a low degree of substitution, when administered to rats, significantly increases short-chain fatty acids (SCFAs), in particular, acetic acid and propionic acid, in the intestines. It has been reported that acetic acid is absorbed at the intestine, transported via the blood vessels, and acts on adipocytes and muscles to restrain fat accumulation, to enhance fat burning, and to restrain obesity (Kimura et al., NATURE COMMUNICATIONS, 4:1829, 2013). It has also been reported that acetic acid passes through the blood-brain barrier and acts on the hypothalamus to restrain appetite (Frost et al., NATURE COMMUNICATIONS, 5:3611, 2014). The short-chain fatty acids have been reported to stimulate enteroendocrine cells via GPR43 receptor to release peptide YY, which is an anorectic hormone (Karaki et al., Cell and Tissue Research, 324, p. 353, 2006). The short-chain fatty acids, in particular propionic acid, have been reported to inhibit biosyntheses of fatty acids and cholesterols in the liver and to lower blood cholesterol and triglyceride levels (Nishina et al., The Journal of Nutrition, 120, 668, 1990; and Hara et al., The Journal of Nutrition, 129, 942, 1999).

Accordingly, the cellulose acetate with a low degree of substitution, when ingested or administered, is expected to have therapeutic and prophylactic effects on obesity and/or hypercholesterolemia.

In addition, the inventors have found that the cellulose acetate with a low degree of substitution, when administered, offers excellent therapeutic and/or prophylactic effects on STAM mice, which are non-alcoholic steatohepatitis model animals.

The inventors have made the present invention on the basis of these findings.

Specifically, the present invention provides a nutrient composition that contains a cellulose acetate having a total degree of acetyl substitution of 0.4 to 1.1.

The cellulose acetate may have a compositional distribution index (CDI) of 2.0 or less, where the compositional distribution index (CDI) is specified as follows:

CDI=(Measured value of half height width of chemical composition)/(Theoretical value of half height width of chemical composition)

where the measured value of half height width of chemical composition represents a half height width of chemical composition determined by HPLC analysis of a cellulose acetate propionate prepared by propionylating all residual hydroxy groups of the cellulose acetate (sample); and the theoretical value of half height width of chemical composition is specified as follows:

$$\text{Theoretical value of half height width of chemical composition} = \frac{2.35482\sqrt{3 \cdot DPw \cdot (DS/3) \cdot (1-DS/3)}}{DPw} \quad [\text{Math. 1}]$$

where DS represents the total degree of acetyl substitution, and DPw represents a weight-average degree of polymerization determined by a GPC-light scattering method using a cellulose acetate propionate prepared by propionylating all residual hydroxy groups of the cellulose acetate (sample).

The present invention also provides a livestock feed that contains a cellulose acetate having a total degree of acetyl substitution of 0.4 to 1.1.

The present invention also provides a lipid metabolism-improving agent that contains a cellulose acetate having a total degree of acetyl substitution of 0.4 to 1.1. The lipid metabolism-improving agent may also be an agent for livestock use.

The present invention further provides a prophylactic and/or therapeutic agent for inflammatory bowel diseases and/or immune disorder, where the agent contains a cellulose acetate having a total degree of acetyl substitution of 0.4 to 1.1. The prophylactic and/or therapeutic agent for inflammatory bowel diseases and/or immune disorder may also be an agent for livestock use.

The present invention further provides a prophylactic and/or therapeutic agent for cancer (malignant tumor), where the agent contains a cellulose acetate having a total degree of acetyl substitution of 0.4 to 1.1. The prophylactic and/or therapeutic agent for cancer may also be an agent for livestock use.

The cancer is preferably selected from the group consisting of liver, colon, mammary, pulmonary, ovarian, prostatic, gastric, and pancreatic cancers.

The present invention also provides a prophylactic and/or therapeutic agent for non-alcoholic steatohepatitis, where the agent contains a cellulose acetate having a total degree of acetyl substitution of 0.4 to 1.1. The prophylactic and/or therapeutic agent for non-alcoholic steatohepatitis may also be an agent for livestock use.

The present invention also provides a prophylactic and/or therapeutic agent for obesity and/or diabetes, where the agent contains a cellulose acetate having a total degree of acetyl substitution of 0.4 to 1.1. The prophylactic and/or therapeutic agent for obesity and/or diabetes may also be an agent for livestock use.

The present invention also provides a prophylactic and/or therapeutic agent for hypercholesterolemia, where the agent contains a cellulose acetate having a total degree of acetyl substitution of 0.4 to 1.1. The prophylactic and/or therapeutic agent for hypercholesterolemia may also be an agent for livestock use.

Advantageous Effects of Invention

The nutrient composition and the livestock feed according to the present invention each contain a cellulose acetate having a low degree of acetyl substitution, which has excellent water solubility or hydrophilicity. The nutrient composition and the livestock feed therefore significantly improve the lipid metabolism and highly effectively lower triglyceride levels. This is probably because the nutrient composition and the livestock feed impede absorption of high-calorie components and fats through the intestinal wall. In addition, the nutrient composition and the livestock feed are intestine friendly, less cause diarrhea, less affect various serum chemical analyses data and have excellent safety, as compared with equivalents containing other water-soluble cellulose derivatives such as CMC.

The lipid metabolism-improving agent and livestock-use lipid metabolism-improving agent according to the present invention have excellent lipid metabolism-improving action and are still highly safe.

The prophylactic and/or therapeutic agent for inflammatory bowel diseases and/or immune disorder according to the present invention is expected to offer excellent prophylactic and/or therapeutic effects on inflammatory bowel diseases and/or immune disorder and are still highly safe.

The prophylactic and/or therapeutic agent for cancer according to the present invention has excellent prophylactic and/or therapeutic effects on cancers and is still highly safe.

The prophylactic and/or therapeutic agent for non-alcoholic steatohepatitis according to the present invention has excellent prophylactic and/or therapeutic effects on non-alcoholic steatohepatitis and is still highly safe.

The prophylactic and/or therapeutic agent for obesity and/or diabetes according to the present invention has excellent prophylactic and/or therapeutic effects on obesity and/or diabetes and is still highly safe.

The prophylactic and/or therapeutic agent for hypercholesterolemia according to the present invention has excellent prophylactic and/or therapeutic effects on hypercholesterolemia and is still highly safe.

DESCRIPTION OF EMBODIMENTS

Figure 1:
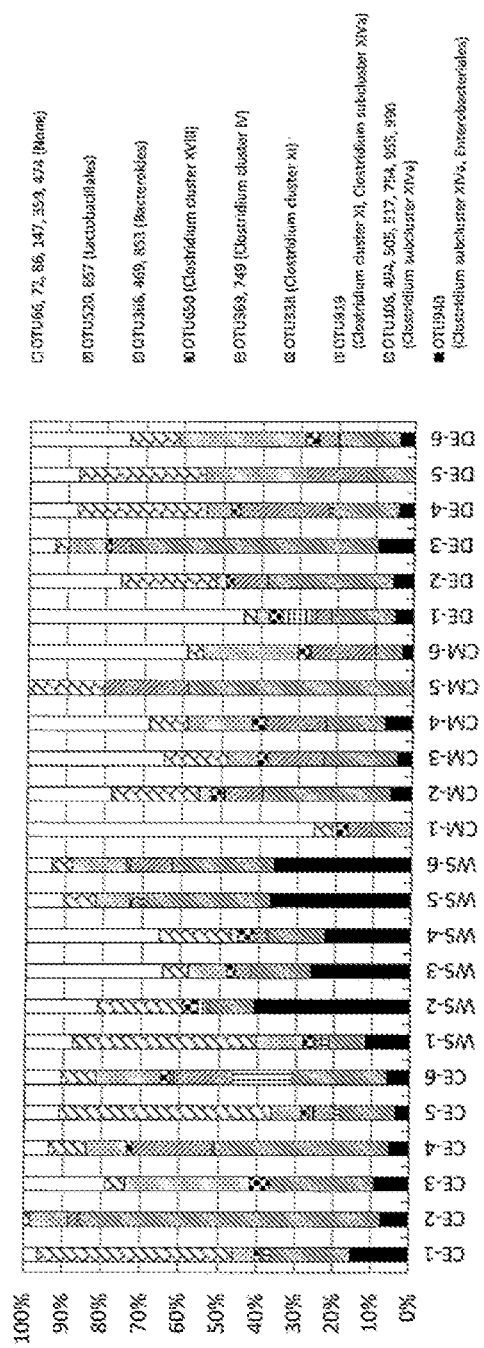
FIG. 1 is a graph illustrating the types and abundances of OTUs in rats fed with feeds in the evaluation test 2 in experimental examples.

According to the present invention, the nutrient composition and the livestock feed, the lipid metabolism-improving agent, the prophylactic and/or therapeutic agent for inflammatory bowel diseases and/or immune disorder, the prophylactic and/or therapeutic agent for cancer, the prophylactic and/or therapeutic agent for non-alcoholic steatohepatitis, the prophylactic and/or therapeutic agent typically for obesity and/or diabetes, and the prophylactic and/or therapeutic agent for hypercholesterolemia each contain a cellulose acetate having a total degree of acetyl substitution of 0.4 to 1.1.

Cellulose Acetate

Total Degree of Acetyl Substitution

The cellulose acetate for use in the present invention has a total degree of acetyl substitution (average degree of acetyl substitution) of 0.4 to 1.1. A cellulose acetate, when having a total degree of acetyl substitution within this range, is highly soluble in water, but, if having a total degree of acetyl substitution out of the range, tends to have inferior solubility in water. The cellulose acetate may have a total degree of acetyl substitution of preferably from 0.5 to 1.0, and more preferably from 0.6 to 0.95. The total degree of acetyl substitution can be measured by a known titrimetry, in which the degree of substitution of a sample cellulose acetate is determined after dissolving the cellulose acetate in water. The total degree of acetyl substitution can also be measured by propionylating hydroxy groups of the cellulose acetate (see the after-mentioned method) to give a cellulose acetate propionate, dissolving the cellulose acetate propionate in deuterated chloroform, and subjecting the same to NMR analysis.

The total degree of acetyl substitution may be determined by determining an acetylation degree according to a method of measuring an acetylation degree prescribed in ASTM D-817-91 (Standard Test Methods of Testing Cellulose Acetates) and converting the acetylation degree into the total degree of acetyl substitution according to a formula below, where this is a most common method for determining the degree of substitution of a cellulose acetate. The formula is expressed as follows:

$$DS = 162.14 \times AV \times 0.01/(60.052 - 42.037 \times AV \times 0.01)$$

where:
  DS represents the total degree of acetyl substitution; and
  AV represents the acetylation degree (%).

Initially, 500 mg of a dried cellulose acetate (sample) is precisely weighed, dissolved in 50 ml of a 4:1 (volume ratio) solvent mixture of ultrapure water and acetone, and combined with 50 ml of a 0.2 N aqueous sodium hydroxide solution, followed by saponification at 25° C. for 2 hours. Next, 50 ml of 0.2 N hydrochloric acid is added, and the amount of eliminated acetic acid is determined by titration with a 0.2 N aqueous sodium hydroxide solution (0.2 N sodium hydroxide normal solution) using phenolphthalein as an indicator. In addition, a blank test is performed in a similar manner, except for using no sample. On the basis of these, the acetylation degree AV (%) is calculated according to the formula:

$$AV (\%) = (A-B) \times F \times 1.201/(\text{Sample weight (g)})$$

where:
  "A" represents the titer (ml) of the 0.2 N sodium hydroxide normal solution;
  "B" represents the titer (ml) of the 0.2 N sodium hydroxide normal solution in the blank test; and
  "F" represents the factor of the 0.2 N sodium hydroxide normal solution.

Compositional Distribution Index (CDI)

The cellulose acetate for use in the present invention may have a compositional distribution (intermolecular distribution of degree of substitution) not limited and may have a compositional distribution index (CDI) of typically 1.0 to 3.0. The cellulose acetate may have a compositional distribution index (CDI) of preferably 1.0 to 2.0, more preferably 1.0 to 1.8, furthermore preferably 1.0 to 1.6, and particularly preferably 1.0 to 1.5.

The lower limit of the compositional distribution index (CDI) is 0. This level can be achieved by special synthesis techniques such as a technique in which the 6-position of a glucose residue alone is selectively acetylated with a selectivity of 100% while no other position is acetylated. However, such synthesis techniques have not yet been known. When hydroxy groups of the glucose residue are acetylated and deacetylated all at the same probability, the compositional distribution index CDI stands at 1.0. However, considerable ways and means are required to approach the ideal state as above in actual cellulose reactions. With a decreasing compositional distribution index (CDI), the cellulose acetate has more uniform compositional distribution (intermolecular substitution degree distribution). Advantageously, the cellulose acetate, when having a uniform compositional distribution, can surely have satisfactory water solubility in a wider range of total degree of substitution, can be uniformly dissolved, does not develop a structural viscosity, and is easy to ingest, as compared with conventional equivalents.

The "compositional distribution index (CDI)" herein is defined as the ratio of the measured value of half height width of chemical composition to the theoretical value of half height width of chemical composition ((Measured value of half height width of chemical composition)/(Theoretical value of half height width of chemical composition)). The "half height width of chemical composition" is also referred to as "half height width of intermolecular substitution degree distribution" or simply to "half height width of substitution degree distribution".

The evaluation of uniformity of the total degree of acetyl substitution of a cellulose acetate can be performed with, as an index, the magnitude of half height width of a maximum peak in an intermolecular substitution degree distribution curve of the cellulose acetate. The "half height width" is also called "half peak width". The "half height width" refers to the width of a chart at a height half the peak height (maximum height) in the chart, in which the chart is plotted with the abscissa (X-axis) indicating a degree of acetyl substitution and the ordinate (Y-axis) indicating an abundance at that degree of acetyl substitution. The half height width is an index indicating how the distribution disperses.

The half height width of substitution degree distribution can be determined by high-performance liquid chromatographic (HPLC) analysis. A way to convert the abscissa (elution time) in an elution curve of a cellulose ester in HPLC into a degree of substitution (0 to 3) is described in Japanese Unexamined Patent Application Publication No. 2003-201301 (paragraphs [0037] to [0040]).

Theoretical Value of Half-Height Width of Chemical Composition

The theoretical value of half height width of chemical composition (half height width of substitution degree distribution) can be calculated stochastically. Specifically, the theoretical value of half height width of chemical composition can be determined according to Formula (1):
[Math. 2]

$$\text{Theoretical value of half height width of chemical composition} = 2.35482\sqrt{mpq}/DPw \quad (1)$$

where:

m represents the total number of hydroxy groups and acetyl groups per molecule of the cellulose acetate;

p represents the probability of substitution of hydroxy group with acetyl group in one molecule of the cellulose acetate;

q=1−p; and

DPw represents the weight-average degree of polymerization as determined by the GPC-light scattering method.

A way to measure the weight-average degree of polymerization (DPw) will be described later.

The theoretical value of half height width of chemical composition represented by Formula (1) is a half height width of chemical composition, which inevitably occurs when all hydroxy groups in a cellulose are acetylated and deacetylated at the same probability, and which is derived in accordance with the so-called binomial theorem. The theoretical value of half height width of chemical composition is expressed by Formula (2) on the basis of the degree of substitution and the degree of polymerization. Formula (2) is defined as a definitional formula to determine the theoretical value of half height width of chemical composition. Formula (2) is expressed as follows:
[Math. 3]

$$\text{Theoretical value of half height width of chemical composition} = 2.35482\sqrt{3*DPw*(DS/3)*(1-DS/3)}/DPw \quad (2)$$

where:

DS represents the total degree of acetyl substitution; and

DPw represents the weight-average degree of polymerization as determined by the GPC-light scattering method.

A way to measure the weight-average degree of polymerization (DPw) will be described later.

To be more exact, Formulae (1) and (2) should take the degree of polymerization distribution into consideration. In this case, "DPw" in Formulae (1) and (2) should be replaced with the function of the degree of polymerization distribution, and the entire formulae should be integrated from a degree of polymerization of 0 to infinity. However, Formulae (1) and (2) give a theoretical value with an approximately sufficient precision, as long as they employ DPw. If a number-average degree of polymerization (DPn) is employed in these formulae, the influence of the degree of polymerization distribution becomes not negligible. To eliminate or minimize this, DPw should be used herein.

Measured Value of Half Height Width of Chemical Composition

The "measured value of half height width of chemical composition" in the present invention refers to a half height width of chemical composition which is obtained by HPLC analysis using a cellulose acetate propionate prepared by propionylating all residual hydroxy groups (unsubstituted hydroxy groups) of a cellulose acetate (sample).

In general, a cellulose acetate having a total degree of acetyl substitution of 2 to 3 can be subjected to a high-performance liquid chromatographic (HPLC) analysis without pretreatment, by which the half height width of chemical composition can be determined. Typically, Japanese Unexamined Patent Application Publication No. 2011-158664 describes a method for analyzing the compositional distribution of a cellulose acetate having a degree of substitution of 2.27 to 2.56.

In contrast, the measured value of half height width of chemical composition (half height width of substitution degree distribution) in the present invention is determined by subjecting residual hydroxy groups in the molecule of the cellulose acetate to derivatization as a pretreatment before HPLC analysis, and then subjecting the derivative to the HPLC analysis. The pretreatment is performed in order to convert the cellulose acetate with a low degree of substitution into a derivative that can be readily dissolved in an organic solvent to enable the HPLC analysis. Specifically, in the present invention, all residual hydroxy groups in the molecule are completely propionylated to give a completely-derivatized cellulose acetate propionate (CAP), and the completely-derivatized cellulose acetate propionate (CAP) is analyzed by HPLC to determine the half height width of chemical composition (measured value). The derivatization herein should be performed completely so that the molecule includes no residual hydroxy group, but acetyl groups and propionyl groups alone. Specifically, the total of the degree of acetyl substitution (DSac) and the degree of propionyl substitution (DSpr) should be 3. This is because a relational expression: DSac+DSpr=3 is used to plot a calibration curve so as to convert the abscissa (elution time) in the HPLC elution curve of the cellulose acetate propionate (CAP) into the degree of acetyl substitution (0 to 3).

The complete derivatization of a cellulose acetate can be performed by allowing propionic anhydride to act upon the cellulose acetate by the catalysis of N,N-dimethylaminopyridine in a pyridine/N,N-dimethylacetamide solvent mixture. More specifically, the cellulose acetate may be subjected to propionylation at a temperature of 100° C. for a reaction time of 1.5 to 3.0 hours, using a 1:1 (v/v) solvent mixture of pyridine and N,N-dimethylacetamide as a solvent in an amount of 20 parts by weight relative to the cellulose acetate (sample), propionic anhydride as a propionylating agent in an amount of 6.0 to 7.5 equivalents relative to hydroxy groups of the cellulose acetate, by the catalysis of N,N-dimethylaminopyridine in an amount of 6.5 to 8.0 mole percent relative to the hydroxy groups of the cellulose acetate. The reaction mixture after the reaction may be subjected to precipitation from methanol as a precipitation solvent and yields a completely derivatized cellulose acetate propionate. Furthermore specifically, 1 part by weight of the reaction mixture is placed into 10 parts by weight of methanol at room temperature to give precipitates, the precipitates are washed with methanol five times, dried at 60° C. in a vacuum for 3 hours, and yields the completely derivatized cellulose acetate propionate (CAP). The aftermentioned polydispersity (Mw/Mn) and weight-average degree of polymerization (DPw) are determined by derivatizing the cellulose acetate (sample) by this method to give a completely derivatized cellulose acetate propionate (CAP), and measuring the parameters using the completely derivatized cellulose acetate propionate (CAP).

The HPLC analysis may be performed in the following manner. Two or more cellulose acetate propionates having different degrees of acetyl substitution as reference standards are subjected to an HPLC analysis using a predetermined measuring apparatus under predetermined measuring conditions, and values of these reference standards measured by the analysis are plotted to give a calibration curve. The calibration curve is a curve indicating a relationship between the elution time and the degree of acetyl substitution (0 to 3) of the cellulose acetate propionates and is generally a cubic curve. On the basis of the calibration curve, the half height width of chemical composition (measured value) of the cellulose acetate (sample) can be determined. What is determined by the HPLC analysis is the relationship between the elution time and the degree of acetyl substitution distribution of cellulose acetate propionates. This is the relationship between the elution time and the degree of acetyl substitution distribution of a substance corresponding to the sample, except with all residual hydroxy groups in the sample molecule being converted into propionyloxy groups. This determination is therefore essentially not different from the determination of the degree of acetyl substitution distribution of the cellulose acetate in the present invention.

The HPLC analysis conditions are as follows:

Apparatus: Agilent 1100 Series

Columns: Waters, Nova-Pak Phenyl 60 Å 4 µm (150 mm in length by 3.9 mm in diameter)+guard column Column temperature: 30° C.

Detector: Varian 380-LC

Injection volume: 5.0 µL (sample concentration: 0.1% (wt/vol))

Eluents: Eluent A: MeOH/$H_2O$=8/1 (v/v), Eluent B: $CHCl_3$/MeOH=8/1 (v/v)

Gradient: A/B=80/20→0/100 (28 min.); Flow rate: 0.7 mL/min.

A substitution degree distribution curve is determined from the calibration curve. This is a substitution degree distribution curve of the cellulose acetate propionate, with the ordinate indicating the abundance of the cellulose acetate propionate and the abscissa indicating the degree of acetyl substitution. The substitution degree distribution curve is also referred to as an "intermolecular substitution degree distribution curve". In the substitution degree distribution curve, a half height width of substitution degree distribution is determined on a maximum peak (E) corresponding to the average degree of substitution in the following manner. Specifically, a base line (A-B) tangent is drawn between a base point (A) at a lower degree of substitution and a base point (B) at a higher degree of substitution of the maximum peak (E). With respect to the base line, a perpendicular line is drawn from the maximum peak (E) toward the abscissa, and an intersection (C) between the perpendicular line and the base line (A-B) is determined. A midpoint (D) between the maximum peak (E) and the intersection (C) is then determined. A line including the midpoint (D) is drawn parallel to the base line (A-B) to determine two intersections (A' and B') of the line and the intermolecular substitution degree distribution curve. From the intersections (A' and B'), perpendicular lines are drawn to the abscissa. The interval between the feet of the thus-drawn perpendicular lines is defined as the half height width of the maximum peak (namely, the half height width of substitution degree distribution).

The half height width of substitution degree distribution as above reflects that the retention times of cellulose acetate propionate molecules contained in the sample vary depending on how hydroxyl groups of glucose rings in individual high-molecular chains constituting the cellulose acetate propionate molecules are acetylated. Therefore, the width of the retention time ideally indicates the width of compositional distribution in the substitution degree unit. However, a high-performance liquid chromatograph includes a duct that does not contribute to the partition (distribution), such as a guide column for protecting the measuring column. The width of retention time often includes an error that is caused not by the width of compositional distribution, but by the configuration of the measuring apparatus. The error is affected typically by the length and inner diameter of the column and by the length and routing of piping from the column to the detector, and varies depending on the configuration of the measuring apparatus, as mentioned above. Thus, the half height width of substitution degree distribution of the cellulose acetate propionate may be determined as a corrected value Z corrected according to a compensation formula. The compensation formula can give a more accurate half height width of substitution degree distribution as a constant or approximately constant value not depending on the type of the measuring apparatus and the measuring conditions. The compensation formula is generally represented by the formula:

$$Z=(X^2-Y^2)^{1/2}$$

where X represents the half height width of substitution degree distribution (uncorrected value) determined with the predetermined measuring apparatus under predetermined measuring conditions; and Y is specified by the formula:

$$Y=(a-b)x/3+b (0 \leq x \leq 3)$$

where "a" represents the apparent half height width of substitution degree distribution of a cellulose acetate having a total degree of substitution of 3 as determined with the same measuring apparatus under the same measuring conditions as in X, where this cellulose acetate does not actually have a substitution degree distribution because of having a total degree of substitution of 3; "b" represents the apparent half height width of substitution degree distribution of a cellulose propionate having a total degree of substitution of 3 as determined with the same measuring apparatus under the same measuring conditions as in X; and "x" represents the total degree of acetyl substitution of the measurement sample ($0 \leq x \leq 3$).

The "cellulose acetate (or cellulose propionate) having a total degree of substitution of 3" refers to a cellulose ester that corresponds to cellulose, except for all hydroxy groups of the cellulose being esterified, and actually (ideally) does not have a half height width of substitution degree distribution (namely, ideally has a half height width of substitution degree distribution of 0).

The cellulose acetate in the present invention may have a measured value of half height width of chemical composition (half height width of substitution degree distribution) of preferably 0.12 to 0.34, and more preferably 0.13 to 0.25.

The above-described theoretical formula of substitution degree distribution gives a stochastically calculated value on the assumption that all acetylation and deacetylation proceed independently and evenly, that is, gives a calculated value according to a binomial distribution. Realistically, however, such ideal situation unlikely occurs. A cellulose ester has a substitution degree distribution significantly wider than one stochastically determined according to the binomial distribution, unless a special scheme is made to allow the hydrolysis reaction of the cellulose acetate to approach the ideal random reaction and/or is made to perform a treatment after the reaction so as to give fractionation in the composition (formulation).

One of possible special schemes for the reaction is exemplified by maintenance of the system under such conditions that deacetylation and acetylation are in equilibrium (are balanced). This scheme, however, is not preferred because the cellulose decomposition proceeds by the acid catalyst in this case. Another example of special schemes for the reaction is employment of such reaction conditions that deacetylation proceeds at a lower rate for a low-substituted cellulose ester. However, no specific method to achieve this has yet been known. Specifically, there is no known special scheme for the reaction to control the substitution degree distribution of a cellulose ester so as to be in accordance with the binomial distribution reaction stochastically. In addition, there occur various circumstances, such as heterogeneity of the acetylation process (cellulose acetylation step) and partial/temporal precipitation by water added stepwise in the ripening process (cellulose acetate hydrolysis process). These circumstances cause the substitution degree distribution to be wider than the binomial distribution. The reality is that it is impossible to avoid all of the circumstances and to achieve the ideal conditions. This resembles that an ideal gas strictly a product of ideals, and an actual gas behaves somewhat differently from the ideal gas.

Conventional techniques relating to the synthesis and treatment of a cellulose acetate with a low degree of substitution have paid little attention to the issues of the substitution degree distribution and have not performed measurement, verification, and consideration of the substitution degree distribution. For example, literature (Journal of the Society of Fiber Science and Technology, Japan, 42, p. 25 (1986)) argues that the solubility of a cellulose acetate with a low degree of substitution is determined by the distribution of acetyl groups to the 2-, 3-, and 6-positions of glucose residue and gives no consideration to the compositional distribution at all.

However, the inventors made investigations and have found that, surprisingly, the substitution degree distribution of a cellulose acetate can be controlled by performing a treatment under adjusted conditions after the cellulose acetate hydrolysis step, as described later. Other literature (CiBment, L., and Rivibre, C., Bull. SOC. chim., (5)1, 1075 (1934); Sookne, A. M., Rutherford, H. A., Mark, H., and Harris, M. J., Research Natl. Bur. Standards, 29, 123 (1942); and A. J. Rosenthal, B. B. White, Ind. Eng. Chem., 1952, 44(11), pp. 2693-2696.) mention that a cellulose acetate having a degree of substitution of 2.3 offers, upon precipitation fractionation, a fractionation depending on the molecular weight and a trivial fractionation accompanied with the degree of substitution (chemical composition). It has not yet been reported that the degree of substitution (chemical composition) as has been found by the inventors can cause a remarkable fractionation. In addition, it has not yet been verified that the substitution degree distribution (chemical composition) of a cellulose acetate with a low degree of substitution can be controlled by dissolution fractionation or precipitation fractionation.

Another scheme found by the inventors so as to narrow the substitution degree distribution is a hydrolysis reaction (ripening reaction) of the cellulose acetate performed at a high temperature of 90° C. or higher (or higher than 90° C.). The conventional techniques fail to make detailed analyses and considerations on the degree of polymerization of a product obtained by a high-temperature reaction, but it has been believed that cellulose decomposition preferentially occurs in such a high-temperature reaction at 90° C. or higher. This view is considered to be an assumption (stereotype) based only on the consideration relating to viscosity. The inventors have found as follows. Assume that, upon hydrolysis to give a cellulose acetate with a low degree of substitution, the reaction of a cellulose acetate is performed in a large amount of acetic acid at a high temperature of 90° C. or higher (or higher than 90° C.), preferably in the presence of a strong acid such as sulfuric acid. In this case, the cellulose acetate does not undergo reduction in degree of polymerization, but undergoes reduction in viscosity with reduction in CDI. Specifically, the inventors have clarified that the reduction in viscosity with the high-temperature reaction is caused not by reduction in degree of polymerization, but by reduction in structural viscosity because of narrowed substitution degree distribution. The cellulose acetate, when hydrolyzed under the conditions, allows the product (cellulose acetate with a low degree of substitution) to have an extremely low CDI and to have significantly better solubility in water. This is because not only a forward reaction, but also a reverse reaction occur upon the hydrolysis. In contrast to this, the cellulose acetate, when hydrolyzed under such conditions for the reverse reaction as to unlikely occur, causes the resulting product to have a wider substitution degree distribution due to various factors and to include cellulose acetates having a total degree of acetyl substitution of less than 0.4 and cellulose acetates having a degree of acetyl substitution of greater than 1.1 in larger contents, both of which are poorly soluble in water. Thus, the resulting cellulose acetate as a whole has lower solubility in water.

Standard Deviation of Degree of Substitution at 2-, 3-, and 6-Positions

The degrees of acetyl substitution at the 2-, 3-, and 6-positions of the glucose ring of the cellulose acetate in the present invention can be measured by NMR technique according to the Tezuka's method in Carbohydr. Res. 273, 83(1995). Specifically, free hydroxy groups of a cellulose acetate sample are propionylated with propionic anhydride in pyridine. The resulting sample is dissolved in deuterated chloroform and subjected to $^{13}$C-NMR spectral measurement. Carbon signals of acetyl group appear in the order of the 2-position, 3-position, and 6-position from a higher magnetic field in a region of from 169 ppm to 171 ppm, and carbonyl carbon signals of propionyl group appear in the same order in a region of from 172 ppm to 174 ppm. The degrees of acetyl substitution at the 2-, 3-, and 6-positions in the glucose ring of the original cellulose diacetate can be determined on the basis of relative abundances between acetyl group and propionyl group at the corresponding positions. The total of the thus-obtained degrees of acetyl substitution at the 2-, 3-, and 6-positions is the "total degree of acetyl substitution". The total degree of acetyl substitution can also be determined in the above manner. The total degree of acetyl substitution can be analyzed not only by $^{13}$C-NMR, but also by $^{1}$H-NMR.

The standard deviation σ of the degrees of substitution at the 2-, 3-, and 6-positions is defined by the formula:

$$\sigma^2 = \frac{1}{n-1} \sum_{i=1}^{n} (x_1 - \bar{x})^2 \qquad [\text{Math. 4}]$$

where:
σ represents the standard deviation;
n is 3;

of $x_i$, $x_1$ represents the degree of substitution at the 2-position, $x_2$ represents the degree of substitution at the 3-position, and $x_3$ represents the degree of substitution at the 6-position; and $\bar{x}$=(Total degree of acetyl substitution)/3.

The cellulose acetate for use in the present invention preferably has a standard deviation of degrees of acetyl substitution at the 2-, 3-, and 6-positions in the glucose ring of 0.08 or less (0 to 0.08). The cellulose acetate, when having a standard deviation of 0.08 or less, is approximately evenly substituted at the 2-, 3-, and 6-positions in the glucose ring and is highly soluble in water.

Polydispersity (Dispersity; Mw/Mn)

The "polydispersity (Mw/Mn) of molecular weight distribution (polymerization degree distribution)" in the present invention refers to a value determined by the GPC-light scattering method using a cellulose acetate propionate prepared by propionylating all residual hydroxy groups of the cellulose acetate (sample).

The cellulose acetate for use in the present invention preferably has a polydispersity (dispersity; Mw/Mn) of from 1.2 to 2.5. The cellulose acetate, when having a polydispersity Mw/Mn within the range, includes molecules of approximately uniform sizes and is highly soluble in water.

The number-average molecular weight (Mn), weight-average molecular weight (Mw), and polydispersity (Mw/Mn) of the cellulose acetate can be determined by known methods using HPLC. The polydispersity (Mw/Mn) of the cellulose acetate in the present invention may be determined in the following manner. The cellulose acetate (sample) is converted into a completely derivatized cellulose acetate propionate (CAP) by a procedure similar to that in the determination of the measured value of half height width of chemical composition, so as to give a measurement sample soluble in an organic solvent. The completely derivatized cellulose acetate propionate (measurement sample) is analyzed by size exclusion chromatography under conditions as follows (GPC-light scattering method):

Apparatus: Shodex GPC SYSTEM-21H;
Solvent: Acetone;
Column: Two GMHxl columns (Tosoh Corporation) with guard columns (TSKgel guardcolumn HXL-H, Tosoh Corporation);
Flow rate: 0.8 ml/min.;
Temperature: 29° C.;
Sample concentration: 0.25% (wt/vol);
Injection volume: 100 µl;
Detector: MALLS (multi-angle light scattering detector) (Wyatt Technology Corporation, DAWN-EOS); and
Reference material for MALLS calibration: PMMA (having a molecular weight of 27600).

Weight-Average Degree of Polymerization (DPw)

The "weight-average degree of polymerization (DPw)" in the present invention refers to a value as determined by the GPC-light scattering method using a cellulose acetate propionate prepared by propionylating all residual hydroxy groups of the cellulose acetate (sample).

The cellulose acetate in the present invention preferably has a weight-average degree of polymerization (DPw) of from 50 to 800. The cellulose acetate, if having an excessively high weight-average degree of polymerization (DPw), may readily have inferior filterability. The cellulose acetate may have a weight-average degree of polymerization (DPw) of more preferably 55 to 700, and furthermore preferably 60 to 600.

The weight-average degree of polymerization (DPw) may be determined in the following manner. The cellulose acetate (sample) is converted into a completely derivatized cellulose acetate propionate (CAP) by a procedure similar to that in the determination of the measured value of half height width of chemical composition. The completely derivatized cellulose acetate propionate is then analyzed by size exclusion chromatography to determine the weight-average degree of polymerization (DPw) (GPC-light scattering method), as in the determination of the polydispersity (Mw/Mn).

The molecular weights (degrees of polymerization) and polydispersity (Mw/Mn) of a water-soluble cellulose acetate are measured by the GPC-light scattering method (e.g., GPC-MALLS or GPC-LALLS), as described above. In this connection, light scattering detection is generally difficult in an aqueous solvent. This is because such aqueous solvent includes a large amount of foreign matter and is liable to be secondarily contaminated even after being once purified. In addition, the aqueous solvent may suffer from unstable spreading of its molecular chain due to an ion dissociative functional group present in a trace amount. Assume that a water-soluble inorganic salt (e.g., sodium chloride) is added to eliminate or minimize this. In this case, the solute may become an unstable dissolution state to form an aggregate or assembly in the resulting aqueous solution. In one of effective methods to avoid this issue, the water-soluble cellulose acetate is derivatized so as to be soluble in an organic solvent, and subjected to GPC-light scattering measurement in the organic solvent, because such an organic solvent contains a small amount of foreign matter and is resistant to secondary contamination. The derivatization of the water-soluble cellulose acetate for this purpose effectively employs propionylation. Specific reaction conditions and aftertreatment are as described in the determination of the measured value of half height width of chemical composition.

Viscosity at 6%

The cellulose acetate in the present invention may have a viscosity at 6% (at 6% concentration) of typically 5 to 500 mPa·s, and preferably 6 to 300 mPa·s. The cellulose acetate, if having an excessively high viscosity at 6%, may have inferior filterability.

The viscosity at 6% of the cellulose acetate can be measured by a method as follows.

An aliquot (3.00 g) of a dried sample is placed in a 50-ml volumetric flask and combined with and dissolved in distilled water to give a 6 wt/vol percent solution. The solution is transferred into a predetermined Ostwald viscometer up to a mark, followed by temperature regulation at 25° C.±1° C. for about 15 minutes. The sample solution is allowed to flow between two marks to measure the time of flow of the solution, and the viscosity at 6% is calculated according to the formula:

$$\text{Viscosity at 6\% (mPa·s)} = C \times P \times t$$

where:
C is the constant of the sample solution;
P is the density (0.997 g/cm$^3$) of the sample solution; and
t is the time in second of flow of the sample solution.

The sample solution constant is determined by measuring the flow time of a standard liquid for calibrating viscometer (trade name JS-200, supplied by SHOWA SHELL SEKIYU K. K. (in conformity with Japanese Industrial Standard (JIS) Z 8809)) by the above procedure, and calculating the constant according to the formula:

$$\text{Sample solution constant} = (\text{Absolute viscosity (mPa·s) of standard solution}) / ((\text{Density (g/cm}^3\text{) of standard solution}) \times (\text{Flow time (second) of standard solution}))$$

Production of Cellulose Acetate with Low Degree of Substitution

The cellulose acetate (cellulose acetate with a low degree of substitution) for use in the present invention may be produced typically by a hydrolysis step (ripening step) (A), a precipitation step (B), and a washing/neutralizing step (C). In the hydrolysis step (A), a cellulose acetate having a medium to high degree of substitution is hydrolyzed. The washing/neutralizing step (C) may be performed as needed.

Hydrolysis Step (Ripening Step) (A)

In this step, a starting-material cellulose acetate is hydrolyzed. The "starting-material cellulose acetate" refers to a cellulose acetate having a medium to high degree of substitution. The cellulose acetate having a medium to high degree of substitution for use as the starting material may have a total degree of acetyl substitution of typically 1.5 to 3, and preferably 2 to 3. The starting-material cellulose acetate may be selected from cellulose diacetates having a total degree of acetyl substitution of 2.27 to 2.56 and cellulose triacetates having a total degree of acetyl substitution of from greater than 2.56 to 3, each of which is commercially available.

The hydrolysis reaction may be performed by allowing the starting-material cellulose acetate to react with water in an organic solvent in the presence of a catalyst (ripening catalyst). The organic solvent is exemplified by acetic acid, acetone, alcohols (e.g., methanol), and solvent mixtures of them. Among them, a solvent containing acetic acid is preferred. The catalyst usable herein may be selected from catalysts generally used as deacetylation catalysts. Among them, sulfuric acid is preferred as the catalyst.

The organic solvent (e.g., acetic acid) may be used in an amount of typically 0.5 to 50 parts by weight, preferably 1 to 20 parts by weight, and more preferably 3 to 10 parts by weight, per 1 part by weight of the starting-material cellulose acetate.

The catalyst (e.g., sulfuric acid) may be used in an amount of typically 0.005 to 1 part by weight, preferably 0.01 to 0.5 part by weight, and more preferably 0.02 to 0.3 part by weight, per 1 part by weight of the starting-material cellulose acetate. The catalyst, if used in an excessively small amount, may cause the hydrolysis to require an excessively long time and may thereby cause the target cellulose acetate to have a lower molecular weight. In contrast, the catalyst, if used in an excessively large amount, may cause a larger variation (dispersion) of the depolymerization rate depending on the hydrolysis temperature and thereby cause a high depolymerization rate even at a relatively low hydrolysis temperature, and this may impede the production of a cellulose acetate having a certain high level of molecular weight.

The water in the hydrolysis step may be used in an amount of typically 0.5 to 20 parts by weight, preferably 1 to 10 parts by weight, and more preferably 2 to 7 parts by weight, per 1 part by weight of the starting-material cellulose acetate. The water may also be used in an amount of typically 0.1 to 5 parts by weight, preferably 0.3 to 2 parts by weight, and more preferably 0.5 to 1.5 parts by weight, per 1 part by weight of the organic solvent (e.g., acetic acid). The water may exist in the whole quantity in the system at the reaction start. However, to eliminate or minimize cellulose acetate precipitation, part of the water to be used may exist in the system at the reaction start, with the remainder being added to the system in one or several batches during the reaction.

The reaction in the hydrolysis step may be performed at a temperature of typically 40° C. to 130° C., preferably 50° C. to 120° C., and more preferably 60° C. to 110° C. In particular, the reaction may be performed at a temperature of 90° C. or higher (or at a temperature higher than 90° C.). In this case, the reaction equilibrium tends to lie toward such a direction that the rate of a reverse reaction (acetylation) relative to a forward reaction (hydrolytic reaction) increases. This narrows the substitution degree distribution and can give a cellulose acetate with a low degree of substitution having a very low compositional distribution index CDI without particular scheming of treatment conditions. The reaction in this case preferably employs a strong acid such as sulfuric acid as the catalyst, and an excess amount of acetic acid as the reaction solvent. Assume that the reaction is performed at a temperature of 90° C. or lower. Even in this case, a cellulose acetate with a low degree of substitution having a very low compositional distribution index CDI can be obtained by performing precipitation in the precipitation step using a solvent mixture including two or more different solvents as a precipitation solvent; and/or by performing precipitation fractionation and/or dissolution fractionation in the precipitation step, as will be described later.

Precipitation Step (B)

In this step, the reaction system after the completion of the hydrolysis reaction is cooled down to room temperature, to which a precipitation solvent is added to precipitate a cellulose acetate with a low degree of substitution. The precipitation solvent usable herein can be selected from organic solvents miscible with water; and organic solvents having high solubility in water. Such solvents are exemplified by ketones such as acetone and methyl ethyl ketone; alcohols such as methanol, ethanol, and isopropyl alcohol; esters such as ethyl acetate; nitrogen-containing compounds such as acetonitrile; ethers such as tetrahydrofuran; and solvent mixtures of them.

The precipitation solvent may be selected from solvent mixtures including two or more different solvents. This offers similar effects to the after-mentioned precipitation fractionation and can give a cellulose acetate with a low degree of substitution having a narrow compositional distribution (intermolecular substitution degree distribution) and a low compositional distribution index CDI. Preferred examples of the solvent mixture include a solvent mixture of acetone and methanol; and a solvent mixture of isopropyl alcohol and methanol.

The cellulose acetate with a low degree of substitution obtained by precipitation may further be subjected to precipitation fractionation (fractional precipitation) and/or dissolution fractionation (fractional dissolution). This can give a cellulose acetate with a low degree of substitution having a narrow compositional distribution (intermolecular substitution degree distribution) and a very low compositional distribution index CDI.

The precipitation fractionation may be performed typically in the following manner. The cellulose acetate with a low degree of substitution (solid) obtained by precipitation is dissolved in water to give an aqueous solution having an appropriate concentration (typically 2 to 10 percent by weight, and preferably 3 to 8 percent by weight). A poor solvent is added to the aqueous solution (or, the aqueous solution is added to the poor solvent), the mixture is held at an appropriate temperature (typically 30° C. or lower, and preferably 20° C. or lower) to precipitate a cellulose acetate with a low degree of substitution as precipitates, and the precipitates are collected. The poor solvent is exemplified by alcohols such as methanol; and ketones such as acetone. The poor solvent may be used in an amount of typically 1 to 10 parts by weight, and preferably 2 to 7 parts by weight, per 1 part by weight of the aqueous solution.

The dissolution fractionation may be performed typically in the following manner. The cellulose acetate with a low degree of substitution (solid) obtained by precipitation or the cellulose acetate with a low degree of substitution (solid) obtained by precipitation fractionation is combined with a solvent mixture of water and an organic solvent (e.g., ketones such as acetone; and alcohols such as ethanol). The mixture is stirred at an appropriate temperature (typically 20° C. to 80° C., and preferably 25° C. to 60° C.) and separated into a dense phase and a dilute phase by centrifugal separation. The dilute phase is combined with a precipitation solvent to give precipitates (solid), and the precipitates are collected. The precipitation solvent is exemplified by ketones such as acetone; and alcohols such as methanol. The solvent mixture of water and the organic solvent may have an organic solvent concentration of typically 5 to 50 percent by weight, and preferably 10 to 40 percent by weight.

Washing/Neutralizing Step (C)

The precipitates (solid) obtained from the precipitation step (B) are preferably washed with an organic solvent (poor solvent). The organic solvent is exemplified by alcohols such as methanol; and ketones such as acetone. The precipitates are also preferably washed and neutralized with an organic solvent containing a basic substance. The organic solvent herein is exemplified by alcohols such as methanol; and ketones such as acetone. The neutralizing step may be performed immediately after the hydrolysis step. In this case, it is preferred to add a basic substance or an aqueous solution of the basic substance to the hydrolysis reaction bath.

The basic substance is exemplified by alkali metal compounds and alkaline earth metal compounds. Non-limiting examples of the alkali metal compounds include alkali metal hydroxides such as sodium hydroxide and potassium hydroxide; alkali metal carbonates such as sodium carbonate and potassium carbonate; alkali metal hydrogencarbonates such as sodium hydrogencarbonate; alkali metal carboxylates such as sodium acetate and potassium acetate; and sodium alkoxides such as sodium methoxide and sodium ethoxide. Non-limiting examples of the alkaline earth metal compounds include alkaline earth metal hydroxides such as magnesium hydroxide and calcium hydroxide; alkaline earth metal carbonates such as magnesium carbonate and calcium carbonate; alkaline earth metal carboxylates such as magnesium acetate and calcium acetate; and alkaline earth metal alkoxides such as magnesium ethoxide. Among them, potassium acetate and other alkali metal compounds are preferred.

The washing (and neutralization) can efficiently remove impurities such as the catalyst (e.g., sulfuric acid) used in the hydrolysis step.

The cellulose acetate with a low degree of substitution obtained in the above manner may be subjected, as needed, to pulverization, sorting, and/or granulation so as to have a particle size controlled within a specific range.

Nutrient Composition and Livestock Feed Having Lipid Metabolism-Improving Action The nutrient composition and livestock feed having lipid metabolism-improving action according to the present invention each contain the cellulose acetate with a low degree of substitution.

Assume that the nutrient composition and livestock feed having lipid metabolism-improving action are ingested. In this case, the cellulose acetate with a low degree of substitution is rapidly decomposed by bacteria to give degradation products. The degradation products in such biodegradation give acetic acid and other acidic components. This allows the enteric environment to be suitable for intestinal bacteria that contribute to the maintenance of the host health; and, in this enteric environment, intestinal bacteria (enteric bacteria) that adversely affect the host health become inferior in numbers. Advantageously, the nutrient composition and livestock feed are therefore intestine friendly, less cause diarrhea even when ingested in large amounts, and have excellent safety including data of serum biochemical analyses. Regarding the intestinal flora (intestinal microbiota), the nutrient composition and livestock feed have the function of increasing the OTU 940 group including advantageous *Clostridium* subcluster XIVa.

In an embodiment, the nutrient composition having lipid metabolism-improving action according to the present invention may include the cellulose acetate with a low degree of substitution and, as needed, any of common foodstuffs and any of various vehicles (supports), excipients, diluents, and other additives which are acceptable as foodstuffs. Non-limiting examples of the other additives include corn starch, alpha-starch, casein, sucrose, soybean oil, cellulose, mineral mix, vitamin mix, L-cystine, choline bitartrate, and t-butylhydroquinone. The nutrient composition may further include any of substances used as components typically for health food. Non-limiting examples of the substances include eggshell calcium, calcium pantothenate, royal jelly, propolis, honey, dietary fibers, *Agaricus*, chitin, chitosan, flavonoids, carotenoids, lutein, Chinese herbal medicines, chondroitin, and various amino acids.

The form of the nutrient composition having lipid metabolism-improving action is not limited and may be selected as appropriate according to the intended use. For example, the nutrient composition may be in any form such as forms of powders, granules, capsules, tablets, gummy candies, gum, candies, pills, tablets, powdered drugs, rods, plates, liquids, emulsions, suspensions, syrups, jelly, cream, ointment, sheets, and troches. Such nutrient compositions in these forms can be prepared by known processes using known devices in the art.

The nutrient composition having lipid-metabolism-improving action according to the present invention may contain the cellulose acetate having a total degree of acetyl substitution of 0.4 to 1.1 (cellulose acetate with a low degree of substitution) in a content of generally 0.1% by weight or more, preferably 0.5% by weight or more, and furthermore preferably 1% by weight or more. The nutrient composition, if containing the cellulose acetate with a low degree of substitution in a content less than 0.1% by weight, may fail to offer lipid metabolism-improving effects satisfactorily.

The nutrient composition having lipid-metabolism-improving action according to the present invention is usable for the purpose of improving lipid metabolism, as a nutrient composition for humans, but also as food or feed for rearing animals (domestic animals) such as livestock (e.g., cattle, pigs, horses, and sheep), poultry (e.g., chickens and ducks), and pet animals (e.g., dogs, cats, monkeys, mice, rats, and guinea pigs). Specifically, the livestock feed containing the cellulose acetate with a low degree of substitution contributes to significantly improved lipid metabolism and remarkably decreased excess triglycerides in the livestock body.

Food and Pharmaceutical Preparations

The nutrient composition having lipid-metabolism-improving action according to the present invention is usable as common food and as foodstuffs and/or beverages to be ingested for the maintenance of health, such as health food, food for specified health uses, dietary supplements, food with nutrient function claims, and nutritional supplement food. The nutrient composition is usable not only as the foodstuffs and/or beverages, but also as pharmaceutical nutrient preparations and/or high-density fluid diets each having lipid metabolism-improving action.

Assume that the nutrient composition having lipid-metabolism-improving action according to the present invention is used as a processed food. The processed food is not limited in type, but is exemplified by foodstuffs and beverages. Non-limiting examples of the foodstuffs include processed fishery products such as "chikuwa" (tube-shaped fish paste cake), "hanpen" (cake of ground fish combined with starch and steamed), and fish sausage; processed agricultural products such as hams; confectioneries such as jelly, candies, gummy candies, chewing gum, cookies, biscuits, and chocolate; dairy products such as cheeses, butter, and yogurt; wheaten products such as bread and cake; noodles such as "soba" (buckwheat noodles) and "udon" (Japanese wheat noodles); and seasoning foodstuffs such as sugar and artificial sweeteners. Non-limiting examples of the beverages include tea, soft drinks (refreshing drinks), juices, alcoholic drinks, and nutrition-supplement drinks.

The nutrient composition having lipid-metabolism-improving action according to the present invention is also usable as pharmaceutical preparations (medicaments). Examples of the pharmaceutical preparations include pharmaceutical nutrient preparations and high-density fluid diets for the prophylaxis and/or treatment of patients suffering from lipid metabolism disorder. Examples of the pharmaceutical preparations also include pharmaceutical preparations that contain the cellulose acetate with a low degree of substitution as an active ingredient and are in the form typically of tablets, capsules, powdered drugs, and syrups.

As used herein, the term "therapy" or "treatment" refers to alleviation or curing of symptom(s) of a target disease and/or alleviation or curing of ancillary symptom therewith. The "therapy" or "treatment" herein also includes the cases where the target disease is not "cured", but the symptom(s) are alleviated (e.g., symptomatic treatments).

Also as used herein, the term "prophylaxis" refers to a process for retarding or preventing the onset of symptom(s) of the target disease (including recurrence of the target disease when the disease has been cured); a process for restraining or inhibiting the subject from acquiring the symptom(s) or disease; or reduction of the risk for the subject of acquiring the symptom(s) or disease.

The cellulose acetate having a total degree of acetyl substitution of 0.4 to 1.1 may be used as intact as the pharmaceutical preparation in the present invention. Where necessary, however, the cellulose acetate may be used in combination with one or more other components to give the pharmaceutical preparation. Non-limiting examples of the other components include vehicles, excipients, diluents, food materials and food additives, pharmaceutical preparations (medicaments), pharmaceutical additives, quasi-drug additives, and any other additives, each of which is pharmaceutically acceptable. The pharmaceutical preparation may be either an oral formulation or a non-oral formulation. The form of the pharmaceutical preparation is not limited, is selectable as appropriate, and may be in powdery form, granular form, or any other form similar to those in the nutrient composition. The pharmaceutical preparation may be produced by methods known in the pharmaceutical area.

Non-limiting examples of the additives include excipients (vehicles) such as corn starch, alpha-starch, lactose, sucrose, maltose, trehalose, cyclic tetrasaccharides, dextrin, starch, crystalline cellulose, sodium hydrogencarbonate, and calcium carbonate; disintegrators such as carboxymethylcellulose, agar, and gelatin powder; binders such as poly(vinyl alcohol)s, methylcellulose, and hydroxypropylcellulose; lubricants such as silica, magnesium stearate, and talc; coating agents such as hydroxypropylmethylcellulose; surfactants; emulsifiers; plasticizers; antiseptic agents (antimicrobial agents); humectants (moisturizers); thickeners; thickening/stabilizing agents; antioxidants; chelating agents; colorants; flavors; acidulants; seasonings; pH adjusters; vitamins; amino acids; minerals; fats and oils; dietary supplements; water-soluble polymers; electrolytes; diluents; water; physiological saline solution; alcohols; organic solvents; and extracts derived from animals and plants.

When the nutrient composition according to the present invention is used as a pharmaceutical preparation, the pharmaceutical preparation may be ingested or administered in such an amount that the amount of the cellulose acetate with a low degree of substitution to be ingested or administered is generally about 1 g to about 100 g, and preferably about 10 g to about 60 g in one or several installments per adult human per day, while the amount may vary depending on the type and pathosis (condition) of the target disease, the age of the subject, and the dosage form. The pharmaceutical preparation (nutrient composition), when to be ingested by rearing animals such as livestock, poultry, and pet animals, may be ingested by incorporating the cellulose acetate with a low degree of substitution into feed so that the intake per day falls within the range. In general, the cellulose acetate may be added in an amount of 0.1 to 10 weight percent, and preferably 1 to 6 weight percent, in terms of feed solids content.

The foodstuffs and pharmaceutical preparations may each, when considered as a composition, contain the cellulose acetate having a total degree of acetyl substitution of 0.4 to 1.1 (cellulose acetate with a low degree of substitution) in a content of generally 0.1% by weight or more, preferably 0.5% by weight or more, and furthermore preferably 1% by weight or more. The foodstuffs and pharmaceutical preparations, if containing the cellulose acetate with a low degree of substitution in a content less than 0.1% by weight, may be hard to offer prophylactic and/or therapeutic effects such as indices for lipid metabolism-improving effects.

Lipid Metabolism-Improving Agent

The lipid metabolism-improving agent according to the present invention contains the cellulose acetate having a total degree of acetyl substitution of 0.4 to 1.1 (cellulose acetate with a low degree of substitution). As described above, the cellulose acetate having a total degree of acetyl substitution of 0.4 to 1.1, when ingested by humans and livestock, exhibits the lipid metabolism-improving action. In addition, the cellulose acetate is intestine friendly, less causes diarrhea even when ingested in a large amount, and is highly safe.

The cellulose acetate having a total degree of acetyl substitution of 0.4 to 1.1 may be used as intact as the lipid metabolism-improving agent according to the present invention. Where necessary, however, the cellulose acetate may be used in combination with one or more other components to give the lipid metabolism-improving agent. Non-limiting examples of the other components include vehicles, excipients, diluents, food materials and food additives, pharmaceutical preparations (medicaments), pharmaceutical additives, quasi-drug additives, and any other additives, each of which is pharmaceutically acceptable. The pharmaceutical preparation (lipid metabolism-improving agent) may be either an oral formulation or a non-oral formulation. The form of the pharmaceutical preparation is not limited, is selectable as appropriate, and may be in powdery form, granular form, or any other form similar to those in the nutrient composition. The pharmaceutical preparation may be produced by methods known in the pharmaceutical area.

Non-limiting examples of the additives include excipients (vehicles) such as corn starch, alpha-starch, lactose, sucrose, maltose, trehalose, cyclic tetrasaccharides, dextrin, starch, crystalline cellulose, sodium hydrogencarbonate, and calcium carbonate; disintegrators such as carboxymethylcellulose, agar, and gelatin powder; binders such as poly(vinyl alcohol)s, methylcellulose, and hydroxypropylcellulose; lubricants such as silica, magnesium stearate, and talc; coating agents such as hydroxypropylmethylcellulose; surfactants; emulsifiers; plasticizers; antiseptic agents (antimicrobial agents); humectants (moisturizers); thickeners; thickening/stabilizing agents; antioxidants; chelating agents; colorants; flavors; acidulants; seasonings; pH adjusters; vitamins; amino acids; minerals; fats and oils; dietary supplements; water-soluble polymers; electrolytes; diluents; water; physiological saline solution; alcohols; organic solvents; and extracts derived from animals and plants.

The lipid metabolism-improving agent according to the present invention may contain the cellulose acetate having a total degree of acetyl substitution of 0.4 to 1.1 (cellulose acetate with a low degree of substitution) in a content of generally 0.1% by weight or more, preferably 0.5% by weight or more, and furthermore preferably 1% by weight or more. The lipid metabolism-improving agent, if containing the cellulose acetate with a low degree of substitution in a content less than 0.1% by weight, may be hard to offer the lipid metabolism-improving effects.

The lipid metabolism-improving agent according to the present invention is applicable not only to humans, but also to rearing animals such as livestock (e.g., cattle, pigs, horses, and sheep), poultry (e.g., chickens and ducks), and pet animals (e.g., dogs, cats, monkeys, mice, rats, and guinea pigs).

The lipid metabolism-improving agent according to the present invention may be ingested or administered in such an amount that the amount of the cellulose acetate with a low degree of substitution to be ingested or administered is generally about 1 g to about 100 g, and preferably about 10 g to about 60 g in one or several installments per adult human per day, while the amount may vary depending on the pathosis (condition), age, and dosage form. The lipid metabolism-improving agent, when to be ingested by rearing animals such as livestock, poultry, and pet animals, may be ingested by incorporating the cellulose acetate with a low degree of substitution into feed so that the intake per day falls within the range. In general, the cellulose acetate may be incorporated in an amount of 0.1 to 10 weight percent, and preferably 1 to 6 weight percent, in terms of feed solids content.

Prophylactic and/or Therapeutic Agent for Inflammatory Bowel Diseases and/or Immune Disorder The prophylactic and/or therapeutic agent for inflammatory bowel diseases and/or immune disorder according to the present invention contains the cellulose acetate having a total degree of acetyl substitution of 0.4 to 1.1 (cellulose acetate with a low degree of substitution).

The prophylactic and/or therapeutic agent for inflammatory bowel diseases and/or immune disorder, when considered as a composition, may contain the cellulose acetate having a total degree of acetyl substitution of 0.4 to 1.1 (cellulose acetate with a low degree of substitution) in a content of generally 0.1 weight percent or more, preferably 0.5 weight percent or more, and more preferably 1 weight percent or more.

The prophylactic and/or therapeutic agent for inflammatory bowel diseases and/or immune disorder according to the present invention is applicable not only to humans, but also to rearing animals such as livestock (e.g., cattle, pigs, horses, and sheep), poultry (e.g., chickens and ducks), and pet animals (e.g., dogs, cats, monkeys, mice, rats, and guinea pigs).

The prophylactic and/or therapeutic agent for inflammatory bowel diseases and/or immune disorder according to the present invention may be ingested or administered in such an amount that the amount of the cellulose acetate with a low degree of substitution to be ingested or administered is generally about 1 g to about 100 g, and preferably about 10 g to about 60 g in one or several installments per adult human per day, while the amount may vary depending on the pathosis, age, and dosage form. The prophylactic and/or therapeutic agent for inflammatory bowel diseases and/or immune disorder, when to be ingested by rearing animals such as livestock, poultry, and pet animals, may be ingested by incorporating the cellulose acetate with a low degree of substitution into feed so that the intake per day falls within the range. In general, the cellulose acetate may be incorporated in an amount of 0.1 to 10 weight percent, and preferably 1 to 6 weight percent, in terms of feed solids content.

As described above, the cellulose acetate having a total degree of acetyl substitution of 0.4 to 1.1 has the function of increasing the advantageous OTU 940 group including *Clostridium* subcluster XIVa in the intestinal flora.

Recently, it has been presented as a research finding that a bacterial group (*Clostridium* subclusters IV, XIVa, and XVIII) including the *Clostridium* subcluster XIVa is expected to have therapeutic and prophylactic effects on inflammatory bowel diseases (such as Crohn disease and ulcerative colitis listed by the Ministry of Health, Labour and Welfare (Japan)) and immune disorder such as allergosis, which are intractable diseases (Nature, 500, 232-236 (2013), 8 Aug. 2013). More specifically, the authors of the article experimentally demonstrated that 17 strains falling within *Clostridium* subclusters IV, XIVa, and XVIII of Clostridia have growth-stimulating activities on regulatory T cells (Treg). On the basis of other experimental results, the authors of the article described the mechanism of growth-stimulation on regulatory T cells by Clostridia as follows. (i) The bacteria produce butyric acid via intestinal fermentation. (ii) Butyric acid inhibits histone deacetylases, and this promotes acetylation of histones. Histones are proteins that coil around the DNA in cell nuclei and are involved in gene expression. The histones, when acetylated, have weakened bonding with the DNA to allow the gene to be readily expressed. (iii) Acetylation of histones are promoted by the mechanism described in (ii) in the Foxp3 gene region in DNAs of immature T cells, where the Foxp3 gene is important for differentiation into Treg cells. Thus, the gene is expressed, and the immature T cells are differentiated into Treg cells. Since the Treg cells are involved in intestinal homeostasis, the authors of the article considered that the findings in the article are helpful from the viewpoints of treatment and prophylaxis of inflammatory bowel diseases (such as Crohn disease and ulcerative colitis listed by the Ministry of Health, Labour and Welfare (Japan)) and immune disorder such as allergosis, which are intractable diseases. In addition, the authors of the article have published experimental results that Treg cells increase twice in number in an experiment using butyrylated starch.

On the basis of the findings presented in the article "Nature, 500, 232-236 (2013), 8 Aug. 2013", the cellulose acetate having a total degree of acetyl substitution of 0.4 to 1.1 (cellulose acetate with a low degree of substitution) has the function of increasing the advantageous OTU 940 group including *Clostridium* subcluster XIVa in the intestinal flora and is highly expected to be efficacious in treatment and prophylaxis of inflammatory bowel diseases and immune diseases such as allergosis via the Treg growth-stimulating activities.

Prophylactic and/or Therapeutic Agent for (Including Malignant Tumor and Malignant Neoplasm)

The prophylactic and/or therapeutic agent for cancer (including malignant tumor and malignant neoplasm) according to the present invention contains the cellulose acetate having a total degree of acetyl substitution of 0.4 to 1.1 (cellulose acetate with a low degree of substitution).

Non-limiting examples of the cancer to be treated or prevented include leukemia, seminoma, melanoma, teratoma, lymphoma, neuroblastoma, glioma, rectal cancer, endometrial cancer, renal cancer, adrenal cancer, thyroid cancer, hematological malignancy, skin cancer, brain cancer, cervical cancer, intestinal cancer, liver cancer, colon cancer, gastric cancer, intestinal cancer, head and neck cancer, gastrointestinal cancer, lymph-node cancer, esophageal cancer, colorectal cancer, pancreatic cancer, otorhinolaryngologic neoplasm, mammary cancer, prostatic cancer, uterine cancer, ovarian cancer, and lung cancer; and metastatic cancers from them. Preferred examples of the cancer to be treated include liver cancer, colon cancer and liver metastasis derived therefrom, mammary cancer, lung cancer, ovarian cancer, prostatic cancer, and gastrointestinal cancer (such as gastric cancer and pancreatic cancer).

The prophylactic and/or therapeutic agent for cancer, when considered as a composition, may contain the cellulose acetate having a total degree of acetyl substitution of 0.4 to 1.1 (cellulose acetate with a low degree of substitution) in a content of generally 0.1 weight percent or more, preferably 0.5 weight percent or more, and more preferably 1 weight percent or more.

The prophylactic and/or therapeutic agent for cancer according to the present invention is applicable not only to humans, but also to rearing animals such as livestock (e.g., cattle, pigs, horses, and sheep), poultry (e.g., chickens and ducks), and pet animals (e.g., dogs, cats, monkeys, mice, rats, and guinea pigs).

The prophylactic and/or therapeutic agent for cancer according to the present invention may be ingested or administered in such an amount that the amount of the cellulose acetate with a low degree of substitution to be ingested or administered is generally about 1 g to about 100 g, and preferably about 10 g to about 60 g in one or several installments per adult human per day, while the amount may vary depending on the cancer type, pathosis, age, and dosage form. The prophylactic and/or therapeutic agent for cancer, when to be ingested by rearing animals such as livestock, poultry, and pet animals, may be ingested by incorporating the cellulose acetate with a low degree of substitution into feed so that the intake per day falls within the range. In general, the cellulose acetate may be incorporated in an amount of 0.1 to 10 weight percent, and preferably 1 to 6 weight percent, in terms of feed solids content.

A recently presented article indicates that bacteria having the OTU 940 contribute to lowered methane levels and increased hydrogen levels in human digestive activity (Hirosaki Med. J. 62:7-17, 2011). As described above, (a composition containing) the cellulose acetate having a total degree of acetyl substitution of 0.4 to 1.1, when administered to humans and livestock, significantly increases bacteria having the OTU 940 in the intestinal flora. Accordingly, administration of the composition containing the cellulose acetate with a low degree of substitution to humans and livestock is expected to contribute to lowered methane gas levels and to lowered greenhouse gas levels. In addition, the administration is considered to increase hydrogen gas and to effectively decrease oxidative stress in the liver. The reduction of oxidative stress in the liver by hydrogen gas is reported in British Journal of Nutrition, 2012, 107, 485-492.

Further, it has been recently reported that bacteria falling within the *Clostridium* cluster XI give carcinogenic secondary bile acids (see Nature, 499, 97-101 (2013), 7 Jul. 2013). The cellulose acetate having a total degree of acetyl substitution of 0.4 to 1.1 (or the composition containing the cellulose acetate), when administered to humans and livestock, significantly decreases *Clostridium* cluster XI in the intestinal flora. Accordingly, the administration of the composition containing the cellulose acetate with a low degree of substitution to humans and livestock is highly expected to effectively restrain the onset of liver cancer.

In contrast, Thomsen-Friedenreich antigen α: TFα) is a carbohydrate antigen that is specifically expressed on cancer cell (tumor cell) surface and is a promising target for cancer therapy. The immunity (anti-TFα antibody) against TFα is often also found in healthy human sera and is considered to play a key role in immune surveillance in cancer (e.g., Springer, Journal of Molecular Medicine, 75, pp. 594-602, 1997; and Kurtenkov, Acta Oncologica, 46, pp. 316-323, 2007). Specifically, TFα (also called "core-1") is known to be expressed on wide-ranging cancer cells and is expected to be a prime target for cancer immunotherapy. For example, TFα is expressed on over 60% of primary colon cancer and over 90% of liver metastases from colon cancer as well as on the majority of the carcinomas of other major indications including mammary, pulmonary, ovarian, prostate, and other gastrointestinal cancers such as gastric and pancreatic carcinomas.

A proposed reason why healthy humans not having TFα-expressing cancer cells can previously have the anti-TFα antibody is that *Bacteroides ovatus*, one of intestinal bacteria, expresses a TFα structure; and on the basis of this, the microorganism, when used, may possibly provide anticancer vaccines (Henderson, Glycobiology, vol. 21, no. 10, p. 1277, 2011). In addition, it has been reported that *Bacteroides xylanisolvens* expresses TFα having higher antigenicity and is useful as a therapeutic agent for cancers (US 2014/0302093 A1).

As described above, (a composition including) the cellulose acetate having a total degree of acetyl substitution of 0.4 to 1.1, when administered to humans and livestock, contributes to significantly increased *Bacteroides xylanisolvens* and *Bacteroides ovatus* in the intestinal flora.

Consequently, the composition including the cellulose acetate with a low degree of substitution, when administered to humans and livestock, is highly expected to offer prophylactic and/or therapeutic effects on the cancers.

Prophylactic and/or Therapeutic Agent for Non-Alcoholic Steatohepatitis

Non-alcoholic fatty liver diseases (NAFLDs) are diseases offering histopathology similar to that in alcoholic liver diseases, although the subject does not have a history of chronic alcohol intake. The non-alcoholic steatosis diseases are roughly classified into simple steatosis and steatohepatitis and occur in about 8% of adult humans. The simple steatosis suffers from fat deposit (lipomatosis) in the liver alone. The steatohepatitis suffers from, in addition to the fat deposit, inflammation and/or fibrosis in the liver. Among them, non-alcoholic steatohepatitis (NASH) is a pathosis under which the liver undergoes inflammation with fatty change and undergoes progressing fibrosis. This can lead to liver cirrhosis and cause hepatocellular carcinoma in the course of time. The NASH occurs in about 1% of adult humans. Neither prophylactic technique nor therapeutic technique for NASH is established at present. Only therapeutic exercise and dietary therapy are performed to improve hepatic steatosis and its background obesity under present circumstances. Demands are made to develop efficacious therapies against NASH.

A proposed conventional theory for NASH pathogenesis is the two-hit theory. This theory indicates that the "first hit" is hepatic steatosis (deposition of triglycerides on hepatic cells), and the subsequent "second hit" is caused by hepatic cell damaging factors to develop NASH. Another recently proposed theory for NASH pathogenesis is the multiple parallel hits hypothesis. This hypothesis indicates that NASH is mainly caused by stimulators of inflammation, such as cytokines and bacteria-associated molecules derived from the intestine and the adipose tissue, and these factors act on the liver and are involved in the NASH pathogenesis not in stages, but concurrently. However, the NASH pathogenesis is not considered to be clarified, and no efficacious therapy has yet been established.

The inventors focused attention on that the cellulose acetate with a low degree of substitution, when administered, changes the intestinal flora to effectively reduce stress on the liver. The inventors administered the cellulose acetate with a low degree of substitution to STAM mice, a NASH animal model, and have found that NASH-specific symptoms are improved. On the basis of this, the inventors have found that the cellulose acetate with a low degree of substitution is useful as a prophylactic and/or therapeutic agent for NASH.

Specifically, the prophylactic and/or therapeutic agent for non-alcoholic steatohepatitis according to the present invention contains the cellulose acetate having a total degree of acetyl substitution of 0.4 to 1.1 (cellulose acetate with a low degree of substitution).

The prophylactic and/or therapeutic agent for non-alcoholic steatohepatitis, when considered as a composition, may contain the cellulose acetate having a total degree of acetyl substitution of 0.4 to 1.1 (cellulose acetate with a low degree of substitution) in a content of generally 0.1 weight percent or more, preferably 0.5 weight percent or more, and more preferably 1 weight percent or more.

The prophylactic and/or therapeutic agent for non-alcoholic steatohepatitis according to the present invention is applicable not only to humans, but also to rearing animals such as livestock (e.g., cattle, pigs, horses, and sheep), poultry (e.g., chickens and ducks), and pet animals (e.g., dogs, cats, monkeys, mice, rats, and guinea pigs).

The prophylactic and/or therapeutic agent for non-alcoholic steatohepatitis according to the present invention may be ingested or administered in such an amount that the amount of the cellulose acetate with a low degree of substitution to be ingested or administered is generally about 1 g to about 100 g, and preferably about 10 g to about 60 g in one or several installments per adult human per day, while the amount may vary depending on the pathosis, age, and dosage form. The prophylactic and/or therapeutic agent for non-alcoholic steatohepatitis, when to be ingested by rearing animals such as livestock, poultry, and pet animals, may be ingested by incorporating the cellulose acetate with a low degree of substitution into feed so that the intake per day falls within the range. In general, the cellulose acetate may be incorporated in an amount of 0.1 to 10 weight percent, and preferably 1 to 6 weight percent, in terms of feed solids content.

Prophylactic and/or Therapeutic Agent for Obesity and/or Diabetes

The inventors have found that the cellulose acetate with a low degree of substitution, when administered to rats, causes significant increase of short-chain fatty acids (SCFAs), in particular acetic acid and propionic acid, in the intestines. It has been reported that acetic acid is absorbed through the intestine, transported via the blood vessels, acts on the adipocytes and muscles to restrain fat accumulation, to enhance fat burning, and to restrain obesity (Kimura et al., NATURE COMMUNICATIONS, 4:1829, 2013). It has also been reported that acetic acid passes through the blood-brain barrier and acts on the hypothalamus to restrain appetite (Frost et al., NATURE COMMUNICATIONS, 5:3611, 2014). The short-chain fatty acids have been reported to stimulate enteroendocrine cells via GPR43 receptor to release peptide YY, which is an anorectic hormone (Karaki et al., Cell and Tissue Research, 324, p. 353, 2006).

On the basis of these, the cellulose acetate with a low degree of substitution, when ingested or administered, is expected to offer therapeutic and prophylactic effects on obesity.

In addition, the inventors have found that the cellulose acetate with a low degree of substitution, when ingested or administered, also contributes to increase of *Akkermansia muciniphila* in the intestinal flora.

*Akkermansia muciniphila* has been reported to offer actions for restraining obesity and type II diabetes in animal trials (Everard, Proceedings of the National Academy of Sciences, vol. 110, no. 22, p. 9066, 2013; Lukovac, mBio, 5(4):e01438-14. doi:10.1128/mBio.01438-14, 2014; and Everard et al., Diabetes, 60, p. 2775, 2011). On the basis of this, the cellulose acetate with a low degree of substitution, when ingested or administered, is expected to offer therapeutic and prophylactic effects typically on obesity and type II diabetes.

Specifically, the prophylactic and/or therapeutic agent for obesity and/or diabetes (in particular, type II diabetes) according to the present invention contains the cellulose acetate having a total degree of acetyl substitution of 0.4 to 1.1 (cellulose acetate with a low degree of substitution).

The prophylactic and/or therapeutic agent for obesity and/or diabetes, when considered as a composition, may contain the cellulose acetate having a total degree of acetyl substitution of 0.4 to 1.1 (cellulose acetate with a low degree of substitution) in a content of generally 0.1 weight percent or more, preferably 0.5 weight percent or more, and more preferably 1 weight percent or more.

The prophylactic and/or therapeutic agent for obesity and/or diabetes according to the present invention is applicable not only to humans, but also to rearing animals such as livestock (e.g., cattle, pigs, horses, and sheep), poultry (e.g., chickens and ducks), and pet animals (e.g., dogs, cats, monkeys, mice, rats, and guinea pigs).

The prophylactic and/or therapeutic agent for obesity and/or diabetes according to the present invention may be ingested or administered in such an amount that the amount of the cellulose acetate with a low degree of substitution to be ingested or administered is generally about 1 g to about 100 g, and preferably about 10 g to about 60 g in one or several installments per adult human per day, while the amount may vary depending on the pathosis, age, and dosage form. The prophylactic and/or therapeutic agent for obesity and/or diabetes, when to be ingested by rearing animals such as livestock, poultry, and pet animals, may be ingested by incorporating the cellulose acetate with a low degree of substitution into feed so that the intake per day falls within the range. In general, the cellulose acetate may be incorporated in an amount of 0.1 to 10 weight percent, and preferably 1 to 6 weight percent, in terms of feed solids content.

Prophylactic and/or Therapeutic Agent for Hypercholesterolemia

It has been reported that short-chain fatty acids, in particular propionic acid, inhibit biosyntheses of fatty acids and cholesterols in the liver to lower blood cholesterol and triglyceride levels (Nishina et al., The Journal of Nutrition, 120, 668, 1990; Hara et al., The Journal of Nutrition, 129, 942, 1999). As described above, the cellulose acetate with a low degree of substitution for use in the present invention, when administered, contributes to significant increase of short-chain fatty acids, in particular propionic acid, in the intestines. Consequently, the cellulose acetate with a low degree of substitution, when ingested or administered, is expected to lower the blood cholesterol and triglyceride levels, because the cellulose acetate increases the propionic acid level in the intestines, which propionic acid is transported into the liver to inhibit biosyntheses of fatty acids and cholesterols.

Specifically, the prophylactic and/or therapeutic agent for hypercholesterolemia according to the present invention contains the cellulose acetate having a total degree of acetyl substitution of 0.4 to 1.1 (cellulose acetate with a low degree of substitution).

The prophylactic and/or therapeutic agent for hypercholesterolemia, when considered as a composition, may contain the cellulose acetate having a total degree of acetyl substitution of 0.4 to 1.1 (cellulose acetate with a low degree of substitution) in a content of generally 0.1 weight percent or more, preferably 0.5 weight percent or more, and more preferably 1 weight percent or more.

The prophylactic and/or therapeutic agent for hypercholesterolemia according to the present invention is applicable not only to humans, but also to rearing animals such as livestock (e.g., cattle, pigs, horses, and sheep), poultry (e.g., chickens and ducks), and pet animals (e.g., dogs, cats, monkeys, mice, rats, and guinea pigs).

The prophylactic and/or therapeutic agent for hypercholesterolemia according to the present invention may be ingested or administered in such an amount that the amount of the cellulose acetate with a low degree of substitution to be ingested or administered is generally about 1 g to about 100 g, and preferably about 10 g to about 60 g in one or several installments per adult human per day, while the amount may vary depending on the pathosis, age, and dosage form. The prophylactic and/or therapeutic agent for hypercholesterolemia, when to be ingested by rearing animals such as livestock, poultry, and pet animals, may be ingested by incorporating the cellulose acetate with a low degree of substitution into feed so that the intake per day falls within the range. In general, the cellulose acetate may be incorporated in an amount of 0.1 to 10 weight percent, and preferably 1 to 6 weight percent, in terms of feed solids content.

EXAMPLES

The present invention will be illustrated in further detail with reference to several examples (experimental examples) below. It should be noted, however, that the examples are by no means intended to limit the scope of the present invention.

Production Example 1

One part by weight of cellulose acetate (trade name L-50, supplied by Daicel Corporation, having a total degree of acetyl substitution of 2.43 and a viscosity at 6% of 110 mPa·s) was combined with 5.1 parts by weight of acetic acid and 2.0 parts by weight of water, stirred at 40° C. for 5 hours, and yielded a seemingly uniform solution. The solution was combined with 0.13 part by weight of sulfuric acid, and the resulting solution was held at 70° C. to perform hydrolysis (partial deacetylation; ripening). During the ripening process, water was added twice to the system. Specifically, 0.67 part by weight of water was added to the system after one hour into the reaction, further 1.67 parts by weight of water was added 2 hours later, and the reaction was continued for further 6 hours. The hydrolysis was performed for a total time of 9 hours. In the hydrolysis, a process from the reaction start to the first water addition is referred to as "first ripening"; a process from the first water addition to the second water addition is referred to as "second ripening"; and a process from the second water addition to the reaction finish (reaction completion) is referred to as "third ripening".

After performing the hydrolysis, the system was cooled down to room temperature (about 25° C.), and the reaction mixture was combined with 15 parts by weight of a 1:2 (by weight) acetone-methanol solvent mixture (precipitant) to form precipitates.

The precipitates were collected and recovered as a wet cake having a solids content of 15% by weight. For washing, the precipitates were combined with 8 parts by weight of methanol and then deliquored to a solids content of 15% by weight. This procedure was repeated three times. The washed precipitates were further washed and neutralized twice with 8 parts by weight of methanol containing 0.004% by weight of potassium acetate, dried, and yielded a water-soluble cellulose acetate.

Measurement of Degree of Substitution (DS)

Unsaturated hydroxy groups of a water-soluble cellulose acetate sample were propionylated according to the Tezuka's method described in Carbohydr. Res. 273, 83(1995). The total degree of acetyl substitution of the propionylated cellulose acetate with a low degree of substitution was determined according to the Tezuka's method (ibid.). Specifically, the sample was analyzed by $^{13}$C-NMR, and the total degree of acetyl substitution was determined on the basis of carbonyl signals of acetyl group appearing at 169 to 171 ppm and carbonyl signals of propionyl group appearing at 172 to 174 ppm. The water-soluble cellulose acetate was found to have a total degree of acetyl substitution of 0.87 as determined in the above manner.

Measurement of Compositional Distribution Index (CDI)

The CDI of a cellulose acetate sample was determined by derivatizing the sample into a propionylated cellulose acetate (cellulose acetate propionate) and analyzing the cellulose acetate propionate by HPLC under conditions as follows:

Apparatus: Agilent 1100 Series
Column: Waters Nova-Pak Phenyl 60 Å 4 μm (150 mm in length by 3.9 mm in diameter) with a guard column
Column temperature: 30° C.
Detector: Varian 380-LC
Injection volume: 5.0 μL (sample concentration: 0.1% (wt/vol))

Fluent: Eluent A: MeOH/H$_2$O=8/1 (v/v), Eluent B: CHCl$_3$/MeOH=8/1 (v/v)

Gradient: A/B=80/20→0/100 (28 min); Flow rate: 0.7 mL/min

Initially, authentic samples having known acetyl DSs (total degrees of acetyl substitution) within the range of from 0 to 3 were subjected to HPLC analyses to plot a calibration curve indicating the relationship between the elution time and the acetyl DS. On the basis of the calibration curve, the elution curve (time vs. detected intensity curve) was converted into a curve of acetyl DS vs. detection intensity (compositional distribution curve). An uncorrected half height width X was determined from the compositional distribution curve, and a corrected half height width Z of compositional distribution was determined according to the expression:

$$Z=(X^2-Y^2)^{1/2}$$

where Y represents an apparatus constant defined by the expression:

$$Y=(a-b)x/3+b$$

where:
"a" represents the X value of the authentic sample having an acetyl DS of 3;
"b" represents the X value of the authentic sample having an acetyl DS of 0; and
"x" represents an acetyl DS of the unknown sample.

The compositional distribution index (CDI) was determined from the corrected half height width Z according to the expression:

$$CDI=Z/Z_0$$

where $Z_0$ represents a compositional distribution formed when acetylation and partial deacetylation in the preparation of all partially substituted cellulose acetates occur at the same probability among all hydroxy groups (or acetyl groups) in all molecules, and is defined by the expression:

$$Z_0=2.35482\sqrt{3*DPw*p*q}/DPw \qquad [\text{Math. 5}]$$

where:
DPw represents the weight-average degree of polymerization;
p=(Acetyl DS of the unknown sample)/3; and
q=1−p The water-soluble cellulose acetate was found to have a CDI of 1.4 as determined in the above manner.

Measurement of Weight-Average Degree of Polymerization (DPw) and Dispersity (DPw/DPn)

The weight-average degree of polymerization and dispersity of the cellulose acetate were determined by converting the cellulose acetate into a propionylated cellulose acetate and subjecting the propionylated cellulose acetate to GPC-light scattering measurement under conditions as follows:
Apparatus: Shodex GPC SYSTEM-21H
Solvent: acetone
Column: two GMHxl columns (Tosoh Corporation) with guard columns (TSKgel guardcolumn HXL-H, Tosoh Corporation)
Flow rate: 0.8 ml/min
Temperature: 29° C.
Sample concentration: 0.25% (wt/vol)
Injection volume: 100 μl
Detector: MALLS (multi-angle light scattering detector) (DAWN-EOS, supplied by Wyatt Technology Corporation)
Standard for MALLS: PMMA (molecular weight: 27600)

The water-soluble cellulose acetate was found to have a DPw of 180 and a DPw/DPn of 1.9 as determined in the above manner.

Example 1

Components including the water-soluble cellulose acetate prepared in Production Example 1 were blended in the formulation given in Table 1 and yielded a powdery nutrient composition having lipid metabolism-improving action.

Comparative Example 1

A purified diet AIN-93G (Journal of Nutrition, Vol. 123, pp. 1939-1951 (1993)) supplied by Hayashibara Biochemical Laboratories, Inc. was used as Comparative Example 1, where the formulation of the purified diet is given in Table 1.

Referential Example 1

Components including an indigestible dextrin PineFibre supplied by Matsutani Chemical Industry Co., Ltd. were blended in the formulation given in Table 1 and yielded a powdery nutrient composition.

Referential Example 2

Components including a carboxymethylcellulose (CMC) (CMC 1220 supplied by Daicel FineChem Ltd.) were blended in the formulation given in Table 1 and yielded a powdery nutrient composition.

Evaluation Test 1: Investigation of Lipid Metabolism-Improving Effects on Rats

Seven-week-old male Wistar rats (purchased from Charles River Laboratories Japan, Inc.) were randomly divided into four groups each including 12 rats and preliminarily fed with the purified diet for one week. After the preliminary feeding, one group was fed continuously with the purified diet, and the other three groups were fed with diets prepared in predetermined formulations respectively from the indigestible dextrin, the water-soluble cellulose acetate, and the carboxymethylcellulose (CMC), each for further 4 weeks. The rats were anesthetized with ether, from which blood was collected via the descending aorta, and the rats were sacrificed and dissected to examine organ weights, serum lipid levels, and other points. The rats were kept on each feed (diet) with free access to water and feed throughout the experimentation period while measuring the body weight and food consumption every three or four days. The rats were dissected after they were fasted overnight.

The triglycerides, total cholesterol, and HDL-cholesterol were measured respectively using the neutral lipid triglyceride assay kit (Triglyceride E-Test Wako, Wako Pure Chemical Industries, Ltd.), the total cholesterol assay kit (Cholesterol E-Test Wako, Wako Pure Chemical Industries, Ltd.), and the HDL-cholesterol assay kit (HDL-cholesterol E-Test Wako, Wako Pure Chemical Industries, Ltd.), each of which was commercially available.

Results are presented in Table 2. Table 2 demonstrates that the nutrient composition having lipid metabolism-improving action according to Example 1 enables significant reduction in blood triglyceride levels.

TABLE 1

| Components | Amount (% by weight) | | | |
|---|---|---|---|---|
| | Comparative Example 1 Purified diet | Referential Example 1 Indigestible dextrin | Example 1 Water-soluble cellulose acetate | Referential Example 2 CMC |
| Corn starch | 39.7486 | 39.7486 | 39.7486 | 39.7486 |
| Alpha-starch | 13.2 | 13.2 | 13.2 | 13.2 |
| Casein | 20 | 20 | 20 | 20 |
| Sucrose | 10 | 10 | 10 | 10 |
| Soybean oil | 7 | 7 | 7 | 7 |
| Cellulose | 5 | 2 | 2 | 2 |
| Mineral mix | 3.5 | 3.5 | 3.5 | 3.5 |
| Vitamin mix | 1 | 1 | 1 | 1 |
| L-Cystine | 0.3 | 0.3 | 0.3 | 0.3 |
| Choline bitartrate | 0.25 | 0.25 | 0.25 | 0.25 |
| t-Butyl-hydroquinone | 0.0014 | 0.0014 | 0.0014 | 0.0014 |
| Indigestible dextrin | 0 | 3 | 0 | 0 |
| Water-soluble cellulose acetate | 0 | 0 | 3 | 0 |
| CMC | 0 | 0 | 0 | 3 |

TABLE 2

| Measurement points | | | Comparative Example 1 Purified diet | | Referential Example 1 Indigestible dextrin | | Example 1 Water-soluble cellulose acetate | | Referential Example 2 CMC | |
|---|---|---|---|---|---|---|---|---|---|---|
| | | | Average | Standard deviation | Average | Standard deviation | Average | Standard deviation | Average | Standard deviation |
| Food consumption | | (g) | 492.9 | 34.4 | 485.7 | 34.3 | 481.0 | 48.4 | 495.9 | 37.4 |
| Body weight | | (g) | 346.9 | 22.5 | 352.9 | 16.4 | 344.9 | 15.3 | 340.3 | 15.0 |
| Organ weight | Liver | (g) | 9.35 | 1.03 | 10.03 | 0.69 | 9.89 | 1.45 | 9.85 | 0.60 |
| | Kidney | (g) | 1.26 | 0.26 | 1.29 | 0.10 | 1.45 | 0.18 | 1.24 | 0.26 |
| | Spleen | (g) | 0.85 | 0.20 | 0.72 | 0.10 | 0.79 | 0.12 | 0.62 | 0.03 |
| Serum lipid levels | Triglycerides | (mg/dL) | 60.7 | 27.2 | 43.6 | 14.0 | 40.8* | 14.0 | 53.1 | 23.3 |
| | Total cholesterol | (mg/dL) | 65.0 | 9.1 | 58.9 | 12.3 | 58.3 | 9.9 | 60.2 | 10.6 |
| | HDL-cholesterol | (mg/dL) | 52.2 | 6.0 | 46.6 | 12.9 | 47.2 | 11.3 | 45.3 | 9.7 |

*: Significant at P < 0.05 vs. Comparative Example 1
**: Significant at P < 0.01 vs. Comparative Example 1

Example 2

A feed was prepared by blending and mixing 100 parts by weight of the AIN-93G purified diet (Journal of Nutrition, Vol. 123, pp. 1939-1951 (1993)) supplied by Hayashibara Biochemical Laboratories, Inc. with 2 parts by weight of the water-soluble cellulose acetate prepared in Production Example 1 and 3 parts by weight of a cellulose (trade name Cellulose Powder, supplied by Oriental Yeast Co., Ltd.). The formulation of the purified diet can be found in Table 1.

Referential Example 3

A feed was prepared by blending and mixing 100 parts by weight of the purified diet AIN-93G (Journal of Nutrition, Vol. 123, pp. 1939-1951 (1993)) supplied by Hayashibara Biochemical Laboratories, Inc. with 5 parts by weight of a cellulose (trade name Cellulose Powder, supplied by Oriental Yeast Co., Ltd.). The formulation of the purified diet can be found in Table 1.

Referential Example 4

A feed was prepared by blending and mixing 100 parts by weight of the purified diet AIN-93G (Journal of Nutrition, Vol. 123, pp. 1939-1951 (1993)) supplied by Hayashibara Biochemical Laboratories, Inc. with 2 parts by weight of carboxymethylcellulose (CMC) (CMC 1220 supplied by Daicel FineChem Ltd.) and 3 parts by weight of a cellulose (trade name Cellulose Powder, supplied by Oriental Yeast Co., Ltd.). The formulation of the purified diet can be found in Table 1.

Referential Example 5

A feed was prepared by blending and mixing 100 parts by weight of the purified diet AIN-93G (Journal of Nutrition, Vol. 123, pp. 1939-1951 (1993)) supplied by Hayashibara Biochemical Laboratories, Inc. with 2 parts by weight of an indigestible dextrin PineFibre supplied by Matsutani Chemical Industry Co., Ltd. and 3 parts by weight of a cellulose (trade name Cellulose Powder, supplied by Oriental Yeast Co., Ltd.). The formulation of the purified diet can be found in Table 1.

Evaluation Test 2: Safety Test and Intestinal Flora Analysis

Four-week-old male Wistar rats (purchased from Charles River Laboratories Japan, Inc.) were habituated for 1 week and were divided into a total of four groups, i.e., a CE group, a CM group, a DE group, and a WS group each including 6 rats and fed for 4 weeks. The "CE group" refers to a cellulose (CE) group and was fed with the feed Referential Example 3. The "CM group" refers to a carboxymethylcellulose (CMC) group and fed with the feed according to Referential Example 4. The "DE group" refers to an indigestible dextrin (DE) group and was fed with the feed according to Referential Example 5. The "WS group" refers to a water-soluble cellulose acetate (WSCA) group and was fed with the feed according to Example 2. The rats were fed at a feeding temperature of 23° C.±2° C. and humidity of 50%±10% with a light-dark cycle of 12 hours, with free access to feed and water.

Safety Test Method

The body weights and food consumptions were recorded throughout the feeding period. After the completion of feeding, the rats were fasted overnight and sacrificed, followed by measurements of organ weights and carcass weight. Serum was collected and subjected to serum biochemical analyses and data analyses. Immediately after the dissection, cecal contents were weighed, diluted with ten times the amount of PBS, and used in intestinal flora analysis mentioned below.

No significant difference was found among the four groups in body weight change, food consumption, and organ weights (cecum, kidney, and liver). In addition, the serum biochemical analysis data revealed that no significant difference was found among the four groups in all the hepatic functions (AST and ALT), renal functions (BUN and CRE), pancreatic functions (GLU), and nutritional conditions (TP and ALB). The results in the body weight change, food consumption, organ weights, and serum biochemical analyses demonstrated that the cellulose acetate having a total degree of acetyl substitution of 0.4 to 1.1 (cellulose acetate with a low degree of substitution), when administered, is superior in safety. In addition, fecal conditions of the rats were observed during the feeding period. As a result, it was found that rats in the CMC group administered with CMC as a water-soluble cellulose derivative developed diarrhea or loose stools, but rats in the WSCA group defecated normal feces. This demonstrated that the cellulose acetate having a total degree of acetyl substitution of 0.4 to 1.1 is also superior in intestinal friendliness with less causing diarrhea, as compared with other water-soluble cellulose derivatives such as CMC.

Intestinal Flora Analysis Method

The intestinal flora was analyzed by the T-RFLP analysis while partially modifying the method of Nagashima et al. (Appl. Environ. Microbiol., 2003, 69:2, 1251-1262). Specifically, the DNA was extracted from 1 ml of the cecum contents diluted with PBS using the DNeasy Blood & Tissue Kit (supplied by QIAGEN). After checking purity, the resulting DNA extract was subjected to PCR. The PCR was performed using a carboxyfluorescein-labeled (FAM-labeled) primer as a fluorescently-labeled primer. A PCR product band of target chain length was cut out via electrophoresis, from which the PCR product was purified using the QIAquick Gel Extraction Kit (supplied by QIAGEN). The purified sample was subjected sequentially to BslI restriction endonuclease treatment and to terminal restriction fragment length polymorphism (T-RFLP) analysis.

The T-RFLP analysis is a technique of analyzing a flora, in which the 16S rRNA gene is treated with restriction endonuclease to give DNA fragments (i.e., OTUs) that are specific among individual bacterial species (or bacterial strains), and the DNA fragments are detected as peaks, and the flora is analyzed based on relative abundances of the individual peaks. Of OTUs, peak positions represent species, and areas represent abundances of the species. Analysis results are presented in Tables 3 to 6 and FIGS. 1 to 4.

Table 3 presents analysis results on types and relative abundances (%) of OTUs, and bacterial specifies estimated based on the OTUs for the rats belonging to the CE, WS, CM, and DE groups, where the OTUs are DNA fragments specificamong bacterial species. In Table 3, numerals (5, 7, 10 . . . ) in the second line each represent an identification number of an individual; and signs (CE-1, CE-2, CE-3 . . . ) in the third line each represent a designation of individual rat, namely, the group name to which the individual belongs, and the identification number of the individual in the group. Numerals in Table 3 each represent the relative abundance (%) of each OTU. FIG. 1 is a bar graph plotted on the basis of data of Table 3, with the abscissa indicating the designation of individual rat and the ordinate indicating the relative abundance (%).

Figure 2:
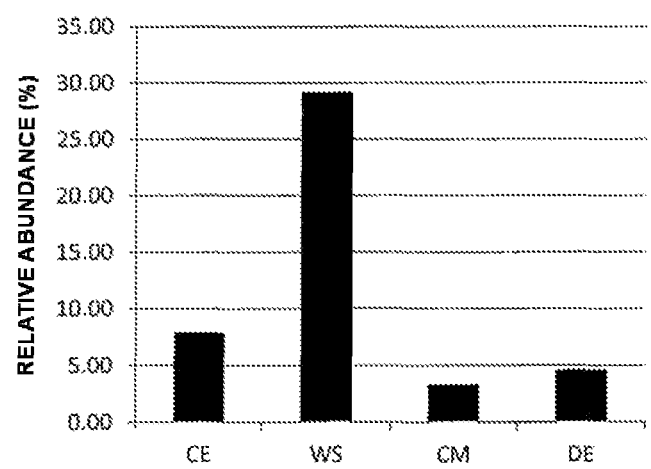
FIG. 2 is a graph illustrating the relative abundance (%) of OTU 940 in experimental groups (CE, WS, CM, and DE) in the evaluation test 2 in the experimental examples.

Table 4 presents the OTU 940 relative abundance (%) in the rats belonging to the CE, WS, CM, and DE groups. FIG. 2 is a bar graph plotted on the basis of data of Table 4, with the abscissa indicating the group name and the ordinate indicating an average of the OTU 940 relative abundance (%) in each group. The OTU 940 is a DNA fragment specific to *Clostridium* subcluster XIVa. As described above, it has been published as research results that bacteria belonging to *Clostridium* subcluster XIVa have therapeutic and prophylactic effects on inflammatory bowel diseases and immune disorder such as allergosis, which are intractable diseases. Table 4 and FIG. 2 demonstrate that the WS group, to which the WSCA (water-soluble cellulose acetate) had been administered, had a remarkably high OTU 940 relative abundance (%) as compared with the CE, CM, and DE groups. This probably indicates remarkable growth of *Clostridium* subcluster XIVa in the intestines. On the basis of this, the administration of the cellulose acetate having a total degree of acetyl substitution of 0.4 to 1.1 (cellulose acetate with a low degree of substitution) is highly expected to have therapeutic and prophylactic effects on inflammatory bowel diseases and immune disorder such as allergosis, which are intractable diseases.

In contrast, the published article indicates that the OTU 940 decreases methane and increases hydrogen in human digestive activities, as described above. The composition containing the cellulose acetate having a total degree of acetyl substitution of 0.4 to 1.1 (cellulose acetate with a low degree of substitution), when administered to humans and livestock, allows the OTU 940 to remarkably increase in the intestinal flora. Thus, the administration of the cellulose acetate having a total degree of acetyl substitution of 0.4 to 1.1 (cellulose acetate with a low degree of substitution) is expected to contribute to decreased methane gas and decreased greenhouse gases and is highly expected to effectively increase hydrogen gas and to thereby decrease oxidative stress on the internal organs.

Figure 3:
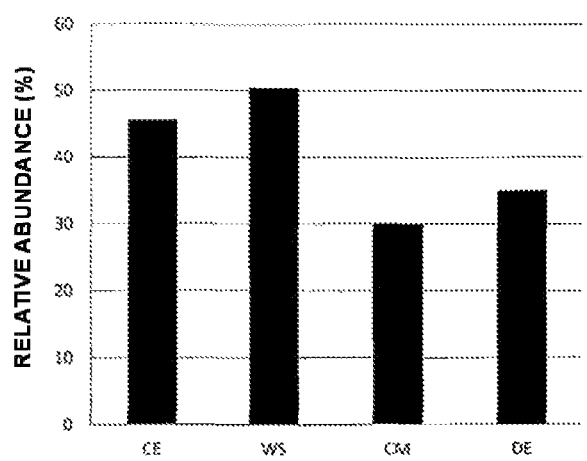
FIG. 3 is a graph illustrating the relative abundance (%) of OUTs that are specific to a bacterial group expected to have therapeutic and prophylactic effects on inflammatory bowel diseases and immune disorder, in the groups (CE, WS, CM, and DE) in the evaluation test 2 in the experimental examples.

Table 5 presents analysis results on relative abundances (%) of OTUs (OTUs 940, 106, 754, 955, 990, 494, 505, 517, 369, 749, and 650) in the rats belonging to the CE, CM, DE, and WS groups. These OTUs are DNA fragments specific to the bacterial groups that are expected to have therapeutic and prophylactic effects on the inflammatory bowel diseases and immune disorder (see Nature, 500, 232-236 (2013), 8 Aug. 2013). In Table 5, numerals (5, 7, 10 . . . ) in the second line each represent an identification number of an individual; and signs (CE-1, CE-2, CE-3 . . . ) in the third line each represent a designation of individual rat, namely, the group name to which the individual belongs, and the identification number of the individual in the group. Numerals in Table 5 each represent the relative abundance (%) of each OTU. FIG. 3 is a bar graph plotted on the basis of data of Table 5, with the abscissa indicating the group name and the ordinate indicating an average of total relative abundances (%) of the specific OTUs in each group. Table 5 and FIG. 3 demonstrate that the WS group, to which the WSCA (water-soluble cellulose acetate) had been administered, had a higher relative abundance (%) of the specific OTUs as compared with the CM and DE groups. This probably indicates remarkable growth of the specific bacteria in the intestines. Also on the basis of this, the administration of the WSCA (water-soluble cellulose acetate) is highly expected to offer therapeutic and prophylactic effects on inflammatory bowel diseases and immune disorder such as allergosis, which are intractable diseases.

Figure 4:
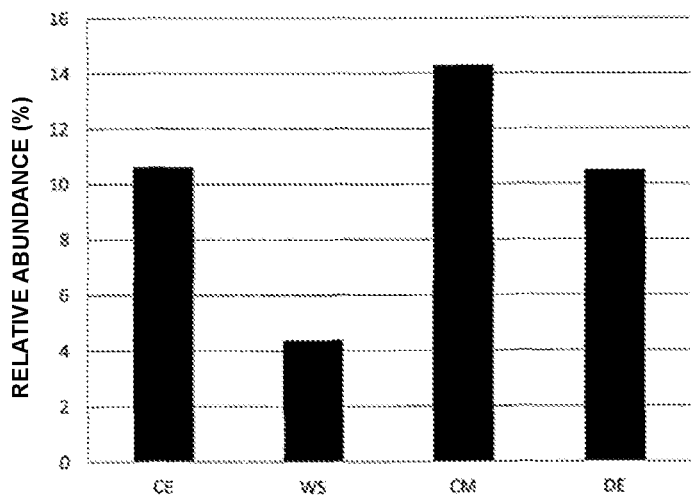
FIG. 4 is a graph illustrating the relative abundance (%) of OUTs specific to a bacterial group that gives carcinogenic secondary bile acids, in the groups (CE, WS, CM, and DE) in the evaluation test 2 in the experimental examples.

Table 6 presents analysis results of the relative abundances (%) of specific OTUs (OTU 919 and OTU 338) for the rats belonging to the CE, CM, DE, and WS groups. The OTU 919 and OTU 338 are DNA fragments specific to the bacteria (*Clostridium* cluster XI) that give carcinogenic secondary bile acids (see Nature, 499, 97-101 (2013), 4 Jul. 2013). In Table 6, numerals (5, 7, 10 . . . ) in the second line each represent an identification number of an individual; and signs (CE-1, CE-2, CE-3 . . . ) in the third line each represent a designation of individual rat, namely, the group name to which the individual belongs, and the identification number of the individual in the group. Numerals in Table 6 each represent the relative abundance (%) of each OTU. FIG. 4 is a bar graph plotted on the basis of data of Table 6, with the abscissa indicating the group name and the ordinate indicating an average of total relative abundances (%) of the specific OTUs in each group. Table 6 and FIG. 4 demonstrate that the WS group, to which the WSCA (water-soluble cellulose acetate) had been administered, had a remarkably low relative abundance (%) of the specific OTUs, as compared with the CE, CM, and DE groups. This probably indicates that the specific bacteria remarkably decrease in the intestines. On the basis of this, the administration of the WSCA (water-soluble cellulose acetate) is expected to have inhibitory or restraining effects on onset of liver cancer.

TABLE 3

| Estimated bacterial taxon | Referential Example 3 | | | | | | Example 2 | | | | | |
|---|---|---|---|---|---|---|---|---|---|---|---|---|
| | 5 CE-1 | 7 CE-2 | 10 CE-3 | 13 CE-4 | 15 CE-5 | 19 CE-6 | 6 WS-1 | 8 WS-2 | 11 WS-3 | 14 WS-4 | 16 WS-5 | 24 WS-6 |
| OTU 940 (*Clostridium* subcluster XIVa, Enterobacteriales) | 15.4 | 7.5 | 9.2 | 5.4 | 3.8 | 6.1 | 11.7 | 41.1 | 26.4 | 22.7 | 37.1 | 36.1 |
| OTUs 106, 494, 505, 517, 754, 955, 990 (*Clostridium* subcluster XIVa) | 21.0 | 77.8 | 27.4 | 45.7 | 14.4 | 24.7 | 9.7 | 11.3 | 15.5 | 14.7 | 32.8 | 26.4 |
| OTU 919 (*Clostridium* cluster XI, *Clostridium* subcluster) | 1.8 | 0.7 | 0.0 | 0.5 | 1.7 | 15.5 | 1.8 | 0.8 | 0.0 | 0.6 | 1.0 | 0.0 |
| OTU 338 (*Clostridium* cluster XI) | 0.7 | 2.6 | 0.0 | 20.6 | 5.2 | 14.3 | 1.5 | 1.0 | 4.2 | 2.8 | 1.8 | 10.7 |
| OTUs 369, 749 (*Clostridium* cluster IV) | 0.0 | 0.0 | 0.0 | 0.0 | 1.2 | 1.8 | 0.4 | 1.3 | 0.0 | 0.4 | 0.0 | 0.0 |
| OTU 650 (*Clostridium* cluster XVIII) | 1.5 | 0.0 | 5.0 | 1.3 | 2.1 | 2.4 | 2.9 | 3.9 | 2.0 | 4.2 | 0.7 | 1.0 |
| OTUs 366, 469, 853 (*Bacteroides*) | 5.7 | 9.7 | 32.2 | 10.5 | 7.9 | 16.7 | 12.4 | 0.0 | 10.0 | 1.8 | 8.6 | 14.0 |
| OTUs 520, 657 (Lactobacillales) | 50.1 | 1.6 | 5.0 | 9.6 | 54.8 | 8.9 | 47.2 | 21.8 | 6.5 | 18.4 | 8.4 | 5.1 |
| OTUs 66, 72, 86, 147, 359, 474 (None) | 3.7 | 0.0 | 21.0 | 6.4 | 8.9 | 9.6 | 12.4 | 18.8 | 35.4 | 34.5 | 9.6 | 6.6 |
| Total | 100 | 100 | 100 | 100 | 100 | 100 | 100 | 100 | 100 | 100 | 100 | 100 |

| Estimated bacterial taxon | Referential Example 4 | | | | | | Referential Example 5 | | | | | |
|---|---|---|---|---|---|---|---|---|---|---|---|---|
| | 1 CM-1 | 3 CM-2 | 12 CM-3 | 17 CM-4 | 18 CM-5 | 23 CM-6 | 2 DE-1 | 4 DE-2 | 9 DE-3 | 20 DE-4 | 21 DE-5 | 22 DE-6 |
| OTU 940 (*Clostridium* subcluster XIVa, Enterobacteriales) | 0.0 | 5.6 | 4.0 | 7.3 | 0.0 | 3.0 | 4.8 | 5.4 | 9.3 | 4.1 | 0.0 | 3.9 |
| OTUs 106, 494, 505, 517, 754, 955, 990 (*Clostridium* subcluster XIVa) | 10.6 | 33.6 | 19.1 | 15.4 | 58.7 | 6.9 | 16.7 | 32.9 | 64.5 | 17.6 | 12.6 | 16.1 |
| OTU 919 (*Clostridium* cluster XI, *Clostridium* subcluster) | 0.0 | 0.3 | 0.0 | 0.0 | 0.0 | 0.0 | 0.0 | 0.3 | 0.0 | 0.8 | 0.0 | 0.3 |
| OTU 338 (*Clostridium* cluster XI) | 6.2 | 9.7 | 15.1 | 15.8 | 21.5 | 17.2 | 4.2 | 8.6 | 4.9 | 23.1 | 15.8 | 4.8 |
| OTUs 369, 749 (*Clostridium* cluster IV) | 0.0 | 0.8 | 0.0 | 0.4 | 0.0 | 0.3 | 9.2 | 0.0 | 0.0 | 0.3 | 0.0 | 0.5 |
| OTU 650 (*Clostridium* cluster XVIII) | 3.0 | 2.5 | 2.5 | 3.1 | 0.0 | 3.0 | 3.3 | 1.9 | 1.5 | 2.0 | 0.0 | 3.2 |
| OTUs 366, 469, 853 (*Bacteroides*) | 1.2 | 3.1 | 7.9 | 16.7 | 0.0 | 24.7 | 3.1 | 2.6 | 9.5 | 6.4 | 26.2 | 32.5 |
| OTUs 520, 657 (Lactobacillales) | 4.7 | 22.6 | 16.2 | 9.9 | 19.9 | 3.7 | 3.2 | 24.3 | 3.4 | 33.3 | 32.7 | 12.8 |
| OTUs 66, 72, 86, 147, 359, 474 (None) | 74.3 | 21.8 | 35.2 | 31.3 | 0.0 | 41.2 | 55.6 | 24.0 | 6.8 | 12.4 | 12.7 | 25.8 |
| Total | 100 | 100 | 100 | 100 | 100 | 100 | 100 | 100 | 100 | 100 | 100 | 100 |

TABLE 4

| | Referential Example 3 | | | | | | Example 2 | | | | | |
|---|---|---|---|---|---|---|---|---|---|---|---|---|
| | Identification number of individual | | | | | | | | | | | |
| | 5 | 7 | 10 | 13 | 15 | 19 | 6 | 8 | 11 | 14 | 16 | 24 |
| Group name | CE-1 | CE-2 | CE-3 | CE-4 | CE-5 | CE-6 | WS-1 | WS-2 | WS-3 | WS-4 | WS-5 | WS-6 |
| OTU 940 | 15.4 | 7.5 | 9.2 | 5.4 | 3.8 | 6.1 | 11.7 | 41.1 | 26.4 | 22.7 | 37.1 | 36.1 |
| Average | | | 7.9 | | | | | | 29.2 | | | |
| SD | | | 4.11 | | | | | | 11 | | | |

| | Referential Example 4 | | | | | | Referential Example 5 | | | | | |
|---|---|---|---|---|---|---|---|---|---|---|---|---|
| | Identification number of individual | | | | | | | | | | | |
| | 1 | 3 | 12 | 17 | 18 | 23 | 2 | 4 | 9 | 20 | 21 | 22 |
| Group name | CM-1 | CM-2 | CM-3 | CM-4 | CM-5 | CM-6 | DE-1 | DE-2 | DE-3 | DE-4 | DE-5 | DE-6 |
| OTU 940 | 0.0 | 5.6 | 4.0 | 7.3 | 0.0 | 3.0 | 4.8 | 5.4 | 9.3 | 4.1 | 0.0 | 3.9 |
| Average | | | 3.3 | | | | | | 4.6 | | | |
| SD | | | 2.96 | | | | | | 2.99 | | | |

TABLE 5

| | | Referential Example 3 | | | | | | Referential Example 4 | | | | | |
|---|---|---|---|---|---|---|---|---|---|---|---|---|---|
| Estimated bacterial taxon | OTU | 5 CE-1 | 7 CE-2 | 10 CE-3 | 13 CE-4 | 15 CE-5 | 19 CE-6 | 1 CM-1 | 3 CM-2 | 12 CM-3 | 17 CM-4 | 18 CM-5 | 23 CM-6 |
| *Clostridium* subcluster XIVa | 940 | 15.4 | 7.5 | 9.2 | 5.4 | 3.8 | 6.1 | 0.0 | 5.6 | 4.0 | 7.3 | 0.0 | 3.0 |
| Enterobacteriales | | | | | | | | | | | | | |
| *Clostridium* subcluster XIVa | 106 | 7.3 | 52.6 | 10.4 | 24.3 | 6.6 | 8.7 | 0.0 | 23.6 | 0.0 | 0.0 | 58.7 | 0.0 |
| *Clostridium* subcluster XIVa | 754 | 0.8 | 4.6 | 1.3 | 1.7 | 0.4 | 0.0 | 3.7 | 0.8 | 4.0 | 5.6 | 0.0 | 1.7 |
| *Clostridium* subcluster XIVa | 955 | 10.0 | 13.3 | 5.3 | 8.4 | 1.8 | 1.8 | 0.0 | 4.5 | 2.5 | 1.4 | 0.0 | 1.8 |
| *Clostridium* subcluster XIVa | 990 | 0.6 | 1.8 | 0.0 | 1.0 | 0.0 | 6.4 | 0.0 | 0.0 | 0.0 | 4.1 | 0.0 | 0.0 |
| *Clostridium* subcluster XIVa | 494 | 1.5 | 3.6 | 8.8 | 6.4 | 3.8 | 4.2 | 4.0 | 2.7 | 5.1 | 2.4 | 0.0 | 2.0 |
| *Clostridium* subcluster XIVa | 505 | 0.2 | 0.0 | 0.0 | 0.0 | 2.8 | 1.1 | 2.7 | 0.0 | 0.6 | 0.0 | 0.0 | 0.0 |
| *Clostridium* subcluster XIVa | 517 | 0.6 | 1.9 | 1.7 | 1.0 | 0.8 | 0.9 | 2.9 | 1.4 | 7.5 | 1.9 | 0.0 | 1.5 |
| *Clostridium* cluster IV | 369 | 0.0 | 0.0 | 0.0 | 0.0 | 1.2 | 1.8 | 0.0 | 0.8 | 0.0 | 0.0 | 0.0 | 0.0 |
| *Clostridium* cluster IV | 749 | 0.0 | 0.0 | 0.0 | 0.0 | 0.0 | 0.0 | 0.0 | 0.0 | 0.0 | 0.4 | 0.0 | 0.3 |
| *Clostridium* cluster XVIII | 650 | 1.5 | 0.0 | 5.0 | 1.3 | 2.1 | 2.4 | 3.0 | 2.5 | 2.5 | 3.1 | 0.0 | 3.0 |
| Total | | 37.9 | 85.3 | 41.7 | 52.4 | 21.6 | 35.0 | 13.6 | 42.5 | 25.6 | 26.2 | 58.7 | 13.2 |

| | | Referential Example 5 | | | | | | Example 2 | | | | | |
|---|---|---|---|---|---|---|---|---|---|---|---|---|---|
| Estimated bacterial taxon | OTU | 2 DE-1 | 4 DE-2 | 9 DE-3 | 20 DE-4 | 21 DE-5 | 22 DE-6 | 6 WS-1 | 8 WS-2 | 11 WS-3 | 14 WS-4 | 16 WS-5 | 24 WS-6 |
| *Clostridium* subcluster XIVa | 940 | 4.8 | 5.4 | 9.3 | 4.1 | 0.0 | 3.9 | 11.7 | 41.1 | 26.4 | 22.7 | 37.1 | 36.1 |
| Enterobacteriales | | | | | | | | | | | | | |
| *Clostridium* subcluster XIVa | 106 | 0.5 | 24.0 | 26.4 | 0.7 | 0.0 | 5.0 | 0.5 | 0.4 | 0.9 | 0.0 | 0.7 | 2.1 |
| *Clostridium* subcluster XIVa | 754 | 0.0 | 1.0 | 0.0 | 0.7 | 0.0 | 1.8 | 0.9 | 0.9 | 1.5 | 3.1 | 4.3 | 0.7 |
| *Clostridium* subcluster XIVa | 955 | 5.0 | 3.8 | 10.2 | 4.3 | 0.0 | 2.6 | 0.7 | 0.5 | 1.0 | 0.4 | 0.3 | 1.3 |
| *Clostridium* subcluster XIVa | 990 | 0.0 | 0.0 | 0.0 | 6.5 | 0.0 | 0.0 | 3.5 | 4.9 | 4.4 | 4.0 | 10.7 | 11.8 |
| *Clostridium* subcluster XIVa | 494 | 10.2 | 2.5 | 24.9 | 2.3 | 3.6 | 5.3 | 3.8 | 3.7 | 7.7 | 6.5 | 16.8 | 8.0 |
| *Clostridium* subcluster XIVa | 505 | 0.0 | 0.3 | 0.0 | 2.0 | 6.2 | 0.7 | 0.0 | 0.5 | 0.0 | 0.0 | 0.0 | 1.6 |
| *Clostridium* subcluster XIVa | 517 | 1.0 | 1.2 | 3.0 | 1.1 | 2.8 | 0.8 | 0.4 | 0.5 | 0.0 | 0.7 | 0.0 | 0.9 |
| *Clostridium* cluster IV | 369 | 9.2 | 0.0 | 0.0 | 0.0 | 0.0 | 0.0 | 0.4 | 1.3 | 0.0 | 0.0 | 0.0 | 0.0 |
| *Clostridium* cluster IV | 749 | 0.0 | 0.0 | 0.0 | 0.3 | 0.0 | 0.5 | 0.0 | 0.0 | 0.0 | 0.4 | 0.0 | 0.0 |
| *Clostridium* cluster XVIII | 650 | 3.3 | 1.9 | 1.5 | 2.0 | 0.0 | 3.2 | 2.9 | 3.9 | 2.0 | 4.2 | 0.7 | 1.0 |
| Total | | 34.0 | 40.2 | 75.4 | 24.0 | 12.6 | 23.8 | 24.7 | 57.6 | 43.9 | 42.0 | 70.6 | 63.6 |

TABLE 6

| | | Referential Example 3 | | | | | | Referential Example 4 | | | | | |
|---|---|---|---|---|---|---|---|---|---|---|---|---|---|
| Estimated bacterial taxon | OTU | 5 CE-1 | 7 CE-2 | 10 CE-3 | 13 CE-4 | 15 CE-5 | 19 CE-6 | 1 CM-1 | 3 CM-2 | 12 CM-3 | 17 CM-4 | 18 CM-5 | 23 CM-6 |
| *Clostridium* cluster XI | 919 | 1.8 | 0.7 | 0.0 | 0.5 | 1.7 | 15.5 | 0.0 | 0.3 | 0.0 | 0.0 | 0.0 | 0.0 |
| *Clostridium* subcluster XIVa | | | | | | | | | | | | | |
| *Clostridium* cluster XI | 338 | 0.7 | 2.6 | 0.0 | 20.6 | 5.2 | 14.3 | 6.2 | 9.7 | 15.1 | 15.8 | 21.5 | 17.2 |
| Total | | 2.5 | 3.3 | 0.0 | 21.1 | 6.9 | 29.8 | 6.2 | 10.0 | 15.1 | 15.8 | 21.5 | 17.2 |

| | | Referential Example 5 | | | | | | Example 2 | | | | | |
|---|---|---|---|---|---|---|---|---|---|---|---|---|---|
| Estimated bacterial taxon | OTU | 2 DE-1 | 4 DE-2 | 9 DE-3 | 20 DE-4 | 21 DE-5 | 22 DE-6 | 6 WS-1 | 8 WS-2 | 11 WS-3 | 14 WS-4 | 16 WS-5 | 24 WS-6 |
| *Clostridium* cluster XI | 919 | 0.0 | 0.3 | 0.0 | 0.8 | 0.0 | 0.3 | 1.8 | 0.8 | 0.0 | 0.6 | 1.0 | 0.0 |
| *Clostridium* subcluster XIVa | | | | | | | | | | | | | |
| *Clostridium* cluster XI | 338 | 4.2 | 8.6 | 4.9 | 23.1 | 15.8 | 4.8 | 1.5 | 1.0 | 4.2 | 2.8 | 1.8 | 10.7 |
| Total | | 4.2 | 8.9 | 4.9 | 23.9 | 15.8 | 5.2 | 3.3 | 1.8 | 4.2 | 3.4 | 2.9 | 10.7 |

EXAMPLE 3

A feed (diet) was prepared by blending components including the water-soluble cellulose acetate prepared in Production Example 1 in the formulation given in Table 7.

EXAMPLE 4

A feed was prepared by blending components including the water-soluble cellulose acetate prepared in Production Example 1 in the formulation given in Table 7.

EXAMPLE 5

A feed was prepared by blending components including the water-soluble cellulose acetate prepared in Production Example 1 in the formulation given in Table 7.

COMPARATIVE EXAMPLE 2

A feed was prepared by blending components in the formulation given in Table 7.

REFERENTIAL EXAMPLE 6

A feed was prepared by blending components including a fructo-oligosaccharide (MEIOLIGO P, Meiji Co., Ltd.) in the formula given in Table 7.

TABLE 7

| Components | Comparative Example 2 | Referential Example 6 | Example 3 | Example 4 | Example 5 |
|---|---|---|---|---|---|
| | Blending amount (weight percent) | | | | |
| Corn starch | 60.25 | 56.25 | 59.25 | 58.25 | 56.25 |
| Milk casein | 25.0 | 25.0 | 25.0 | 25.0 | 25.0 |
| Corn oil | 5.0 | 5.0 | 5.0 | 5.0 | 5.0 |
| Mineral mix [1] | 3.5 | 3.5 | 3.5 | 3.5 | 3.5 |
| Vitamin mix [1] | 1.0 | 1.0 | 1.0 | 1.0 | 1.0 |
| Choline bitartrate | 0.25 | 0.25 | 0.25 | 0.25 | 0.25 |
| Cellulose | 5.0 | 5.0 | 5.0 | 5.0 | 5.0 |
| Water-soluble cellulose acetate | 0.0 | 0.0 | 1.0 | 2.0 | 4.0 |
| Fructo-oligosaccharide | 0.0 | 4.0 | 0.0 | 0.0 | 0.0 |
| Total | 100.0 | 100.0 | 100.0 | 100.0 | 100.0 |

[1] Formulation of AIN-76 (supplied by Oriental Yeast Co., Ltd.)

Evaluation Test 3: Analyses of Short-Chain Fatty Acid Level in Cecal Contents and of Flora As animal trials, thirty (30) seven-week-old male Wistar rats (weighed 150 to 170 g) (Japan SLC, Inc., Haruno branch) were each individually kept in a stainless cage at a room temperature of 24° C.±1° C. and relative humidity of 55%±5% with a light-dark cycle of 12 hours (lighted: 7:00 (7 a.m.) to 19:00 (7 p.m.)). The rats after carrying in were inhabited by feeding with the feed prepared in Comparative Example 2 and tap water for 3 days. After the habituation, the rats were divided on a basis of body weight into five groups, i.e., a control (Cont) group, a 4% FOS group, a 1% WSCA group, a 2% WSCA group, and a 4% WSCA group. The control (Cont) group refers to a group fed with the experimental feed prepared in Comparative Example 2. The 4% FOS group refers to a group fed with the experimental feed prepared in Referential Example 6. The 1% WSCA group refers to a group fed with the experimental feed prepared in Example 3. The 2% WSCA group refers to a group fed with the experimental feed prepared in Example 4. The 4% WSCA group refers to a group fed with the experimental feed prepared in Example 5. The rats in the groups were fed with the feeds and tap water for 21 days with free access to feed and water. All the groups each include six rats. On the final day, all the day's feces were collected and subjected to measurements.

The body weights and food consumptions were measured throughout the feeding period.

After the completion of feeding, the six rats per each group were sacrificed and dissected at 10:30 without fasting. The dissection was performed under anesthesia with pentobarbital. The blood was collected from the abdominal aorta, and the cecum was isolated and colonic contents were collected. After weighing, the isolated cecum was dissected, from which contents were collected. The collected contents were subjected to measurements of pH (with Horiba Compact pH Meter), and short-chain fatty acids.

Table 8 represents the food consumption and body weight increase (gram per 21 days), the cecal tissue weight and the cecal contents amount (each in gram), and the pH of the cecum, colon, and feces.

TABLE 8

| | Cont. | 1% WSCA | 2% WSCA | 4% WSCA | FOS |
|---|---|---|---|---|---|
| Food consumption (g/21 days) | 349 | 341 | 328* | 331* | 323 |
| Body weight increase (g/21 days) | 92 | 88 | 89 | 82 | 87 |
| Cecum | | | | | |
| Tissue weight (g) | $0.5^c$ | $0.6^c$ | $0.7^b$ | $0.8^a$ | 0.8 |
| Contents amount (g) | $2.7^c$ | $2.8^c$ | $4.0^b$ | $5.5^a$ | 5.2 |
| pH | | | | | |
| Cecum | 7.9 | 7.7* | $7.0^{*\dagger}$ | $6.4^{*\dagger\ddagger}$ | 6.4 |
| Colon | $8.1^b$ | $7.2^a$ | $6.6^a$ | $6.6^a$ | 6.7 |
| | (3/6) | (4/6) | (5/6) | (5/6) | |
| Feces | $8.3^b$ | $8.3^b$ | $7.4^a$ | $7.0^a$ | 7.6 |

Significantly different when indicated with different letters of alphabet;
*$p < 0.05$ (vs. Cont.),
†$p < 0.05$ (vs. 1% WSCA),
‡$p < 0.05$ (vs. 2% WSCA)

The rats in the 2% WSCA group and 4% WSCA group were found to tend to have lower food consumptions and lower body weight increases. This is probably because short-chain fatty acids increased in amount in the intestines and restrained the appetite, as described later. The rats in the 1% WSCA, 2% WSCA, 4% WSCA, and 4% FOS groups were found to have increased cecal tissue weight and increased cecal contents amount and lower pH of the cecum, colon, and feces. This is probably because the short-chain fatty acids increased in amount in the intestines, as described later.

Measurement of Short-Chain Fatty Acids Amount in Cecal Contents

Figure 5:
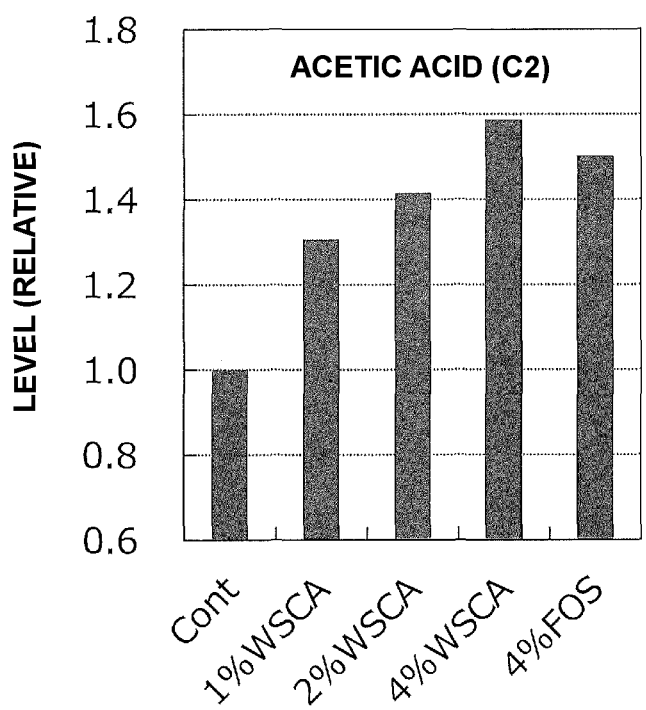
FIG. 5 is a graph illustrating relative acetic acid levels in the cecal contents of rats belonging to experimental groups (1% WSCA, 2% WSCA, 4% WSCA, and 4% FOS groups) in an evaluation test 3 in the experimental examples, where the measured value of a control (Cont) group is set at "1"
Figure 6:
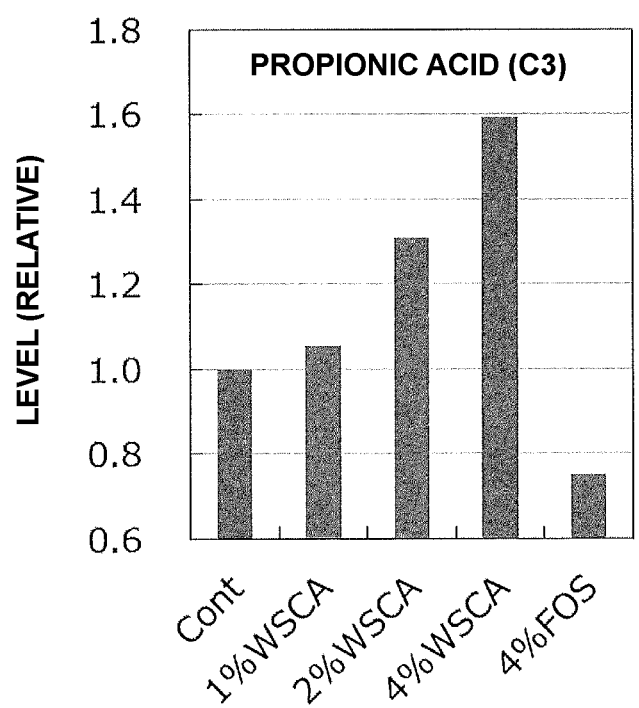
FIG. 6 is a graph illustrating relative propionic acid levels in the cecal contents of the rats belonging to the groups (1% WSCA, 2% WSCA, 4% WSCA, and 4% FOS groups) in the evaluation test 3 in the experimental examples, where the measured value of the control (Cont) group is set at "1"
Figure 7:
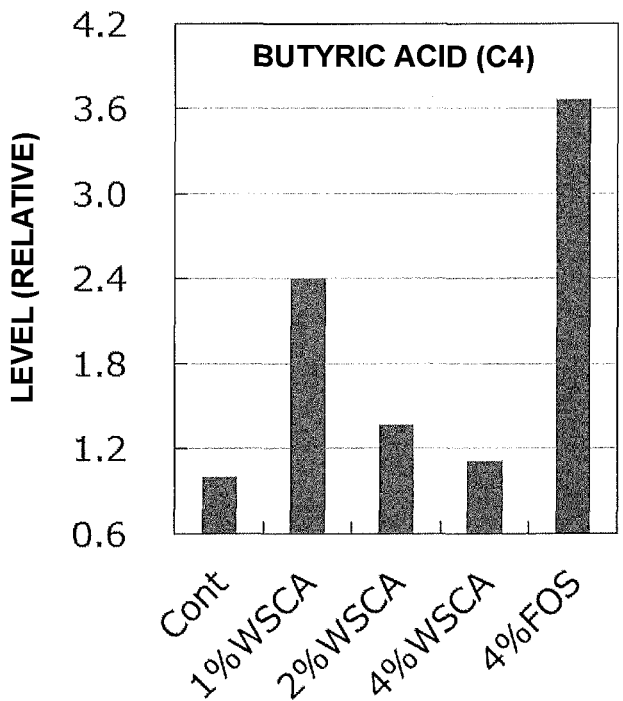
FIG. 7 is a graph illustrating relative butyric acid levels in the cecal contents of the rats belonging to the groups (1% WSCA, 2% WSCA, 4% WSCA, and 4% FOS groups) in the evaluation test 3 in the experimental examples, where the measured value of the control (Cont) group is set at "1"

The cecal contents (about 150 mg) were combined with distilled water so as to give a total weight of 0.5 g, followed by stirring on a vortex mixer. The mixture was combined with 0.5 mL of an internal standard crotonic acid (0.15 mg/mL) in a 5 mM NaOH solution, homogenized using the POLYTRON homogenizer at a level of 30 for 30 seconds with cooling in ice, and centrifugally separated (15000 g, 4° C., 15 minutes). The supernatant (0.5 mL) was transferred to a new Eppendorf tube, combined with equal parts of chloroform, stirred on a vortex mixer for one minute, and further centrifugally separated (15000 g, 4° C., 15 minutes). The aqueous layer (1 mL) was collected in a syringe, the syringe was equipped with a syringe filter (Dismic-13HP) and a needle (23-25 G), and the aqueous layer was transferred to an autosampler vial while taking care not to cause the air to enter the vial bottom. The vial was loaded in an autosampler of HPLC to measure the amounts of acetic acid, propionic acid, and butyric acid, which are short-chain fatty acids. FIGS. 5 to 7 are bar graphs illustrating the relative levels (concentrations) of the short-chain fatty acids assuming that the measured value of the control (Cont) group is set at "1".

FIGS. 5 to 7 demonstrated that the water-soluble cellulose acetate and the fructo-oligosaccharide, when administered, increase the short-chain fatty acids, in particular acetic acid and propionic acid, in the cecum significantly and dose-dependently.

It has been reported that acetic acid is absorbed through the intestine, transported via the blood vessels, acts on the adipocytes and muscles to restrain fat accumulation, to enhance fat burning, and to restrain obesity (Kimura et al., NATURE COMMUNICATIONS, 4:1829, 2013). It has also been reported that acetic acid passes through the blood-brain barrier and acts on the hypothalamus to restrain appetite (Frost et al., NATURE COMMUNICATIONS, 5:3611, 2014).

On the basis of these, the water-soluble cellulose acetate with a low degree of substitution, when ingested or administered, is expected to offer therapeutic and prophylactic effects on obesity.

Plasma Cholesterol Measurement

Figure 8:
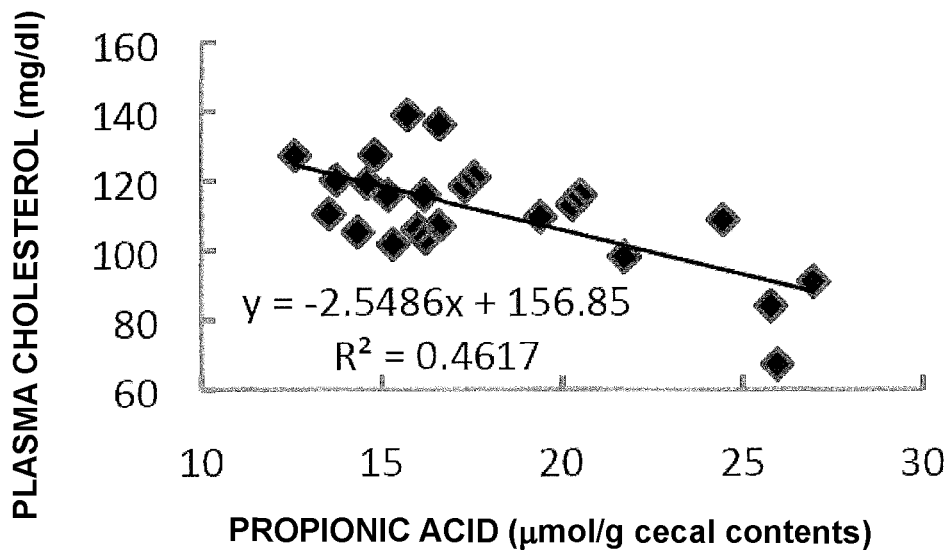
FIG. 8 is a graph plotted with the abscissa indicating the propionic acid level ($\mu$mol/g) in the cecal contents and the ordinate indicating the plasma cholesterol level (mg/dl), for individuals belonging to the groups (control (Cont), 1% WSCA, 2% WSCA, 4% WSCA, and 4% FOS groups) in the evaluation test 3 in the experimental examples.

It has been reported that short-chain fatty acids, in particular propionic acid, inhibit biosyntheses of fatty acids and cholesterols in the liver to lower blood cholesterol and triglyceride levels (Nishina et al., The Journal of Nutrition, 120, 668, 1990; and Hara et al., The Journal of Nutrition, 129, 942, 1999). Plasma cholesterol levels were measured in order to determine how propionic acid affects the biosynthesis of cholesterols in the liver, where the propionic acid is increased in the cecum by the administration of the cellulose acetate with a low degree of substitution. Specifically, the plasma was separated from the above-collected rat blood according to a common procedure, and plasma cholesterol levels of the groups were measured using the Cholesterol C-Test Wako (Wako Pure Chemical Industries, Ltd.). Results are presented in Table 9 below. The results are also plotted as a graph in FIG. 8, with the abscissa indicating the propionic acid level ($\mu$mol/g) in the cecal contents of individuals belonging to the groups, and the ordinate indicating the plasma cholesterol level (mg/dl).

TABLE 9

Plasma Cholesterol

| | Cont. | 1% WSCA | 2% WSCA | 4% WSCA | FOS |
|---|---|---|---|---|---|
| Level (mg/dl) | 122.6 ± 5.0$^a$ | 114.6 ± 4.8$^{ab}$ | 110.6 ± 1.9$^{ab}$ | 96.3 ± 8.2$^b$ | 106.2 ± 7.2 |

Significantly different when indicated with different letters of alphabet (p < 0.05).

The administration of the cellulose acetate with a low degree of substitution lowered the plasma cholesterol level dose-dependently. The administration in the 4% WSCA group offered greater cholesterol lowering action as compared with the group administered with the fructo-oligosaccharide. The plasma cholesterol level was found to tend to lower depending on the propionic acid level in the cecal contents (correlation coefficient $R^2=0.4617$). This suggested that cholesterol biosynthesis inhibition by propionic acid lowers the plasma cholesterol level.

Flora Analysis on Cecal Contents

The cecal contents of the control (Cont) group, 4% WSCA group, and 4% FOS group were each diluted with ten times the amount of PBS, and the florae in the cecal contents were analyzed according to the method of Takahashi et al. (the method described in PLOS ONE, 2014, 9(8), e105592), except for searching the Apollon database instead of the Ribosomal Database Project database (RDP database) for bacteria. The proportions (%) of detected bacterial species are presented in Table 10.

TABLE 10

Bacterial species (%) in cecal contents of rats after 3-week feeding (Tukey-Kramer's test)

| Species | Cont | 4% WSCA | 4% FOS |
|---|---|---|---|
| [Ruminococcus] gnavus | 0.8 $^a$ | 0.6 $^a$ | 0.2 $^a$ |
| Akkermansia muciniphila | 3.7 $^a$ | 9.8 $^a$ | 5.9 $^a$ |
| Anaerostipes caccae | 0.0 $^a$ | 0.0 $^a$ | 6.1 $^a$ |
| Bacteroides acidifaciens | 1.9 $^a$ | 0.0 $^b$ | 0.0 $^b$ |
| Bacteroides ovatus | 0.0 $^a$ | 12.0 $^b$ | 0.0 $^a$ |
| Bacteroides sartorii | 22.8 $^a$ | 3.1 $^b$ | 2.3 $^b$ |
| Bacteroides xylanisolvens | 0.0 $^a$ | 18.3 $^b$ | 0.0 $^a$ |
| Bifidobacterium animalis subsp. animalis | 0.0 $^a$ | 1.8 $^a$ | 27.3 $^b$ |
| Blautia faecis | 2.8 $^a$ | 0.0 $^a$ | 0.0 $^a$ |
| Blautia glucerasea | 2.6 $^{ab}$ | 1.3 $^a$ | 8.2 $^b$ |
| Blautia schinkii | 0.9 $^a$ | 3.7 $^a$ | 0.2 $^a$ |
| Blautia stercoris | 3.2 $^a$ | 2.7 $^a$ | 1.3 $^a$ |
| Clostridium bolteae | 0.4 $^a$ | 2.2 $^{ab}$ | 4.9 $^b$ |
| Clostridium hylemonae | 2.2 $^a$ | 1.2 $^a$ | 0.3 $^a$ |
| Clostridium scindens | 0.4 $^a$ | 0.9 $^a$ | 0.7 $^a$ |
| Lactobacillus gasseri | 0.5 $^a$ | 2.1 $^a$ | 0.7 $^a$ |
| Parabacteroides goldsteinii | 1.2 $^a$ | 1.5 $^a$ | 0.2 $^a$ |
| Rothia nasimurium | 1.2 $^a$ | 0.9 $^a$ | 0.3 $^b$ |
| Ruminococcus bromii | 3.7 $^a$ | 0.9 $^a$ | 0.2 $^a$ |
| Streptococcus sanguinis | 0.7 $^a$ | 0.5 $^{ab}$ | 0.2 $^b$ |
| Unclassified, others | 50.8 | 36.6 | 41.0 |

Significantly different at p < 0.05 when indicated with a superscript including no identical letter of alphabet.

Table 10 demonstrated that the water-soluble cellulose acetate with a low degree of substitution, when administered, increased *Bacteroides xylanisolvens*, *Bacteroides ovatus*, and *Akkermansia muciniphila*. In particular, the water-soluble cellulose acetate, when administered, significantly increased *Bacteroides xylanisolvens* and *Bacteroides ovatus* 1500 times and 1200 times, respectively, as compared with the control (Cont) group, which levels are significantly higher even as compared with the fructo-oligosaccharide-administered group (FOS group) as presented in Table 11 below, where the fructo-oligosaccharide is believed to improve the intestinal flora.

TABLE 11

Percentages (%) of *Bacteroides xylanisolvens* and *Bacteroides ovatus* in the cecal contents of rats after 3-week feeding

| Bacterial species | Control group | 4% WSCA group | 4% FOS group |
|---|---|---|---|
| B. xylanisolvens | $1.3 \times 10^{-2}$ | $1.8 \times 10^{1}$ (1500 times as compared with Control group) | $4.3 \times 10^{-2}$ (3.4 times as compared with Control group) |
| B. ovatus | $9.7 \times 10^{-3}$ | $1.2 \times 10^{1}$ (1200 times as compared with Control group) | $2.9 \times 10^{-2}$ (3.0 times as compared with Control group) |

It has been reported that *Bacteroides xylanisolvens* and *Bacteroides ovatus* express Thomsen-Friedenreich antigen (TF$\alpha$), which is considered to be a promising target for cancer therapy, on cell surface, and these are useful as cancer therapeutic agents (e.g., US 2014/0302093 A1; and Henderson, Glycobiology, vol. 21, no. 10, p. 1277, 2011).

The water-soluble cellulose acetate with a low degree of substitution, when ingested or administered, significantly increases *Bacteroides xylanisolvens* and *Bacteroides ovatus* in the intestines and is therefore expected to offer therapeutic and prophylactic effects, through acquisition of the immunity for TF$\alpha$, on cancers expressing TF$\alpha$, in particular, colon cancer, liver metastases cancers, as well as mammary, pulmonary, ovarian, prostate, and other gastrointestinal cancers such as gastric and pancreatic cancers.

In addition, *Akkermansia muciniphila* has been reported to offer anti-obesity action and type II diabetes-restraining action in animal trials (Everard, Proceedings of the National Academy of Sciences, vol 0.110, no. 22, p. 9066, 2013; Lukovac et al., mBio, 5(4):e01438-14.doi:10.1128/mBio.01438-14, 2014; and Everard et al., Diabetes, 60, p. 2775, 2011). This indicates that the microbe can be a promising target for therapy and/or prophylaxis of obesity and its associated metabolic diseases. On the basis of this, the water-soluble cellulose acetate with a low degree of substitution, when ingested or administered, increases the proportion of *Akkermansia muciniphila* in the intestines and is thereby expected to offer therapeutic and prophylactic effects on obesity and/or type II diabetes.

EXAMPLE 6

A feed was prepared by blending and mixing 100 parts by weight of the AIN-93G purified diet supplied by Oriental Yeast Co., Ltd. with 1 part by weight of the water-soluble cellulose acetate prepared in Production Example 1 and 4 parts by weight of a cellulose (trade name Cellulose Powder, supplied by Oriental Yeast Co., Ltd.). The formulation of the purified diet can be found in Table 1.

EXAMPLE 7

A feed was prepared by blending and mixing 100 parts by weight of the AIN-93G purified diet supplied by Oriental Yeast Co., Ltd. with 2 parts by weight of the water-soluble cellulose acetate prepared in Production Example 1 and 3 parts by weight of a cellulose (trade name Cellulose Powder, supplied by Oriental Yeast Co., Ltd.). The formulation of the purified diet can be found in Table 1.

EXAMPLE 8

A feed was prepared by blending and mixing 100 parts by weight of the AIN-93G purified diet supplied by Oriental Yeast Co., Ltd. with 3 parts by weight of the water-soluble cellulose acetate prepared in Production Example 1 and 2 parts by weight of a cellulose (trade name Cellulose Powder, supplied by Oriental Yeast Co., Ltd.). The formulation of the purified diet can be found in Table 1.

REFERENTIAL EXAMPLE 7

A feed was prepared by blending and mixing 100 parts by weight of the AIN-93G purified diet supplied by Oriental Yeast Co., Ltd. with 5 parts by weight of a cellulose (trade name Cellulose Powder, supplied by Oriental Yeast Co., Ltd.). The formulation of the purified diet can be found in Table 1.

Evaluation Test 4: Influence of Water-Soluble Cellulose Acetate Administration on Body Weight and Serum Biochemical Analysis Data Four-week-old male Wistar rats (purchased from Charles River Laboratories Japan, Inc.) were preliminarily fed with the AIN-93G purified diet supplied by Oriental Yeast Co., Ltd. for one week, where the formulation of the purified diet can be found in Table 1. After the preliminary feeding, the rats were randomly divided into four groups each including 6 rats, i.e., a CE group, a WS 1% group, a WS 2% group, and a WS 3% group, and fed with the above prepared feeds for 4 weeks. Specifically, the CE, WS 1%, WS 2%, and WS 3% groups were fed with the feeds prepared respectively in Referential Example 7, Example 6, Example 7, and Example 8. The rats were fed at a feeding temperature of 23° C.±2° C., humidity of 50%±10%, with a light-dark cycle of 12 hours, with free access to feed and water.

Body Weight and Serum Biochemical Analysis Data

The body weights and food consumptions were recorded during the feeding period. After the completion of feeding, the rats were fasted overnight, sacrificed, and dissected, and the body weights upon dissection and the carcass weights were measured. The serum was collected and subjected to analyses of serum biochemical analysis data on aspartate aminotransferase (AST) and alanine aminotransferase (ALT) as indices for hepatic functions; urea nitrogen (BUN) and creatinine (CRE) as indices for renal functions; total cholesterol (TCHO), HDL cholesterol (HDLC), and triglycerides (TG) as indices for lipid metabolism; albumin (ALB) and total protein (TP) as indices for nutritional conditions; and blood glucose level (GLU), using the FUJI DRI-CHEM (FUJIFILM Corporation).

Figure 9:
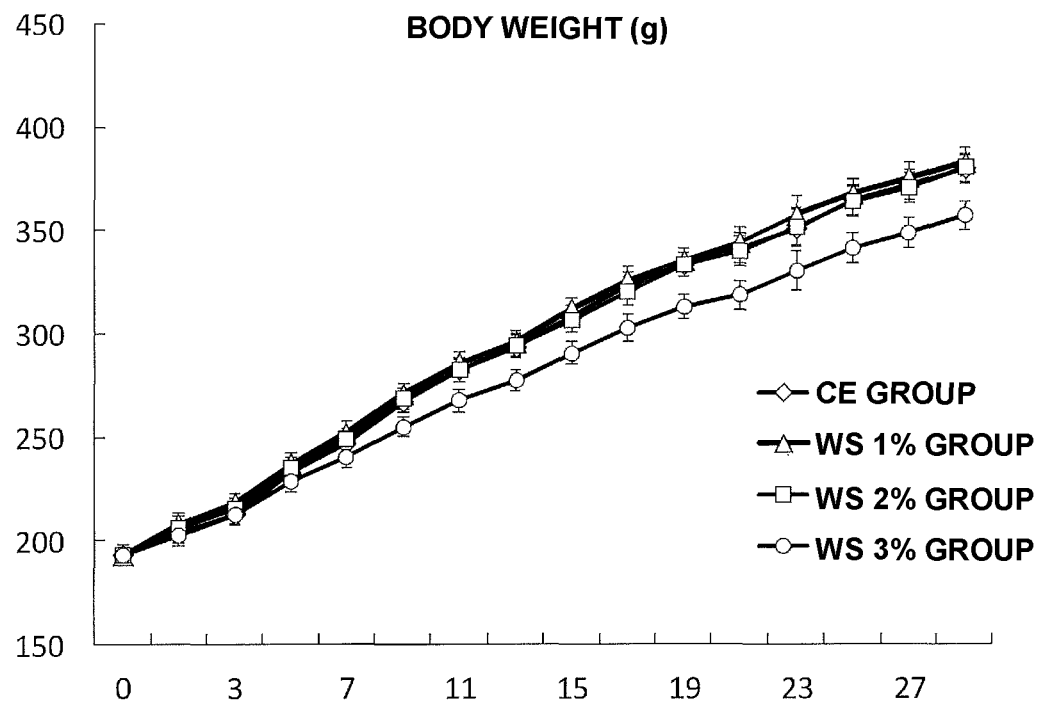
FIG. 9 is a graph illustrating the change in body weight increase of rats belonging to experimental groups (CE, WS 1%, WS 2%, and WS 3% groups) in the evaluation test 4 in the experimental examples.
Figure 10:
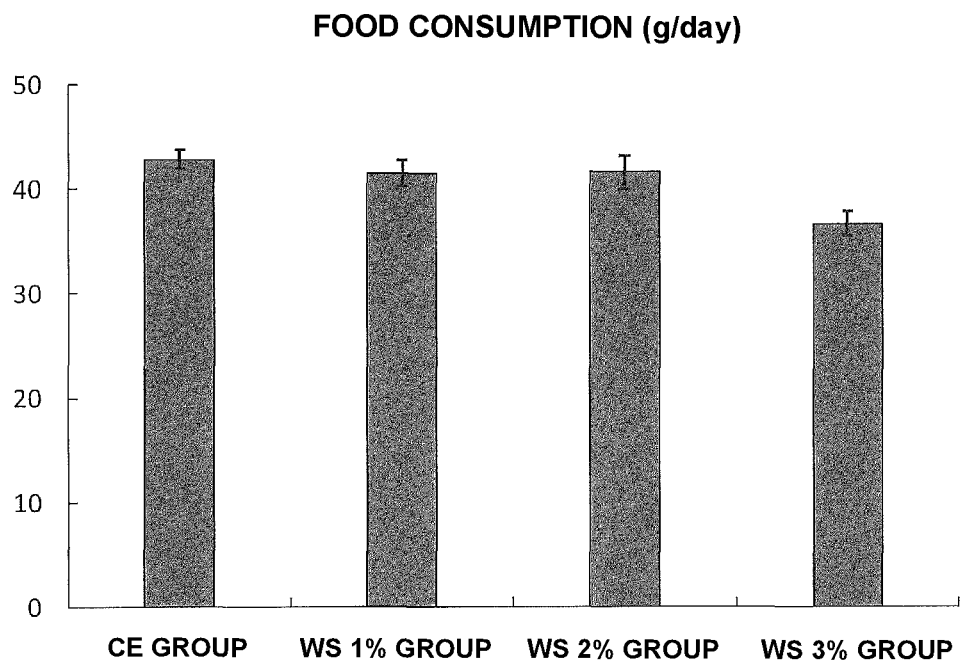
FIG. 10 is a graph illustrating food consumptions (food intakes) (g/day) of the rats belonging to the groups (CE, WS 1%, WS 2%, and WS 3% groups) in the evaluation test 4 in the experimental examples.
Figure 11:
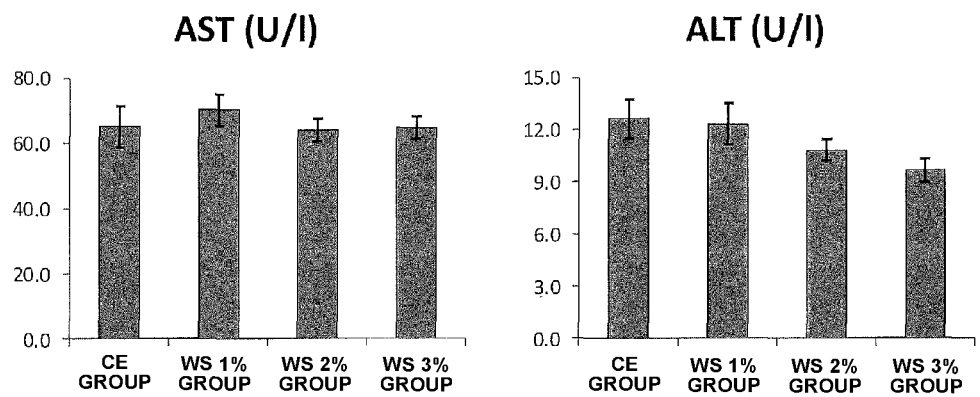
FIG. 11 depicts graphs illustrating serum biochemical analysis data (AST and ALT), as indices for hepatic functions, of the groups (CE, WS 1%, WS 2%, and WS 3% groups) in the evaluation test 4 in the experimental examples.
Figure 12:
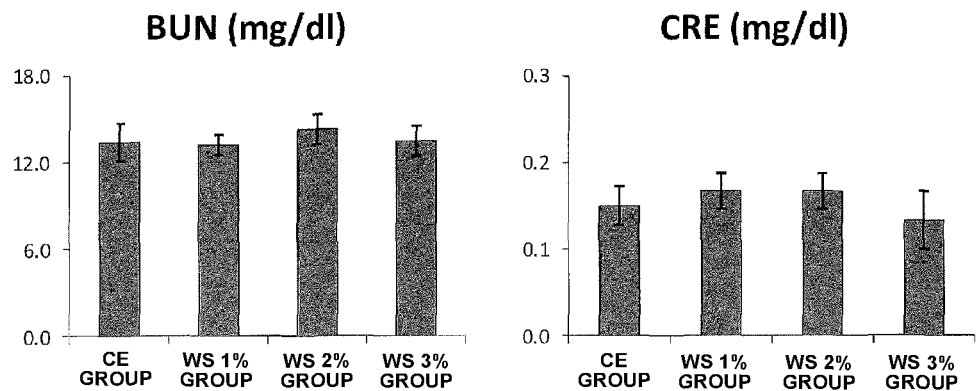
FIG. 12 depicts graphs illustrating serum biochemical analysis data (BUN and CRE), as indices for renal functions, of the groups (CE, WS 1%, WS 2%, and WS 3% groups) in the evaluation test 4 in the experimental examples.
Figure 13:
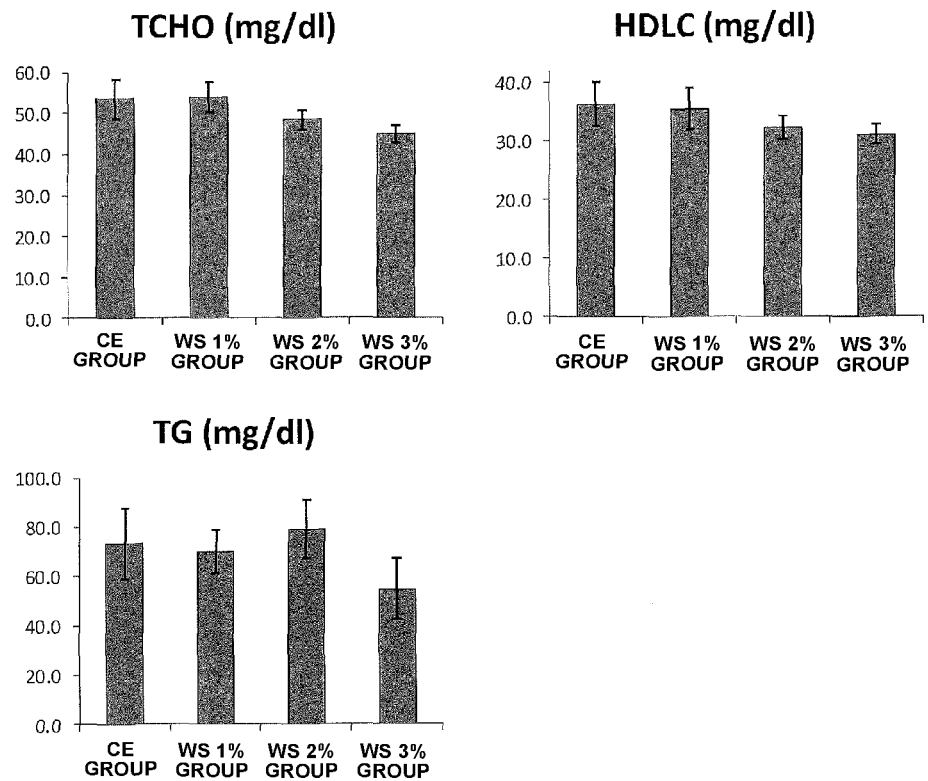
FIG. 13 depicts graphs illustrating serum biochemical analysis data (TCHO, HDLC, and TG), as indices for lipid metabolism, of the groups (CE, WS 1%, WS 2%, and WS 3% groups) in the evaluation test 4 in the experimental examples.
Figure 14:
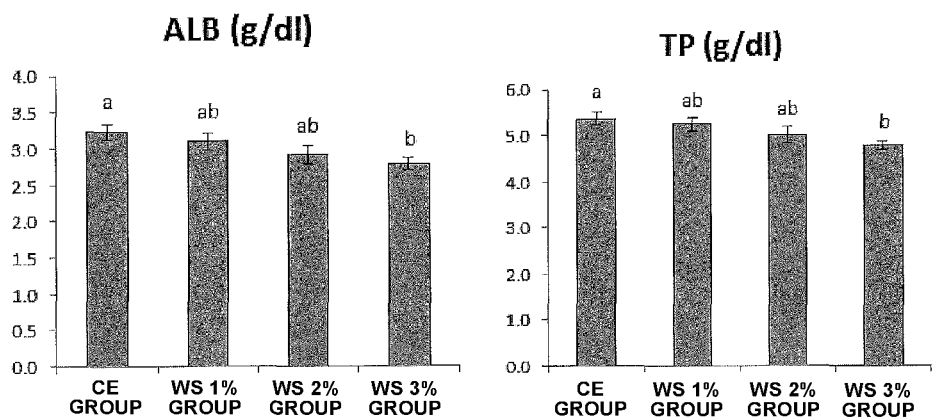
FIG. 14 depicts graphs illustrating serum biochemical analysis data (ALB and TP), as indices for nutritional conditions, of the groups (CE, WS 1%, WS 2%, and WS 3% groups) in the evaluation test 4 in the experimental examples, where data with different letters of alphabet have a significant difference ($p<0.05$) from each other.
Figure 15:
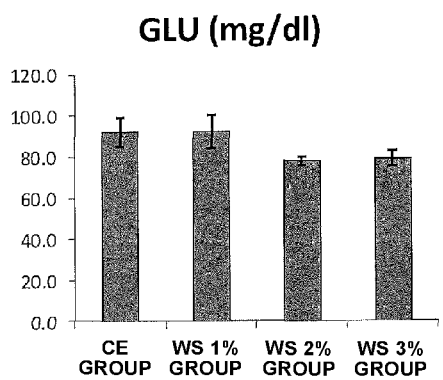
FIG. 15 is a graph illustrating serum biochemical analysis data (GLU), as a blood glucose level, of the groups (CE, WS 1%, WS 2%, and WS 3% groups) in the evaluation test 4 in the experimental examples.

FIG. 9 is a graph illustrating the change in body weight (g); FIG. 10 is a graph illustrating the food consumption (g/day); FIG. 11 is a graph illustrating the AST (U/l) and ALT (U/l) data as indices for hepatic functions; FIG. 12 depicts graphs illustrating BUN (mg/dl) and CRE (mg/dl) data as indices for renal functions; FIG. 13 depicts graphs illustrating TCHO (mg/dl), HDLC (mg/dl), and TG (mg/dl) data as indices for lipid metabolism; FIG. 14 depicts graphs illustrating ALB (g/dl) and TP (g/dl) data as indices for nutritional conditions; and FIG. 15 depicts a graph illustrating GLU (mg/dl) data.

The WS 3% group was found to tend to have lower body weight increase and lower food consumption. This is probably because the ingestion of the water-soluble cellulose acetate increases the amounts of short-chain fatty acids, in particular acetic acid, in the intestines to reduce the body weight increase and the appetite, as described above. In addition, the data indicated that the water-soluble cellulose acetate, when ingested in amounts approximately as in the WS 1% group and the WS 2% group, do not significantly affect the hepatic functions and the renal functions.

The lipid metabolism-related data and the blood glucose level tended to be decreased with an increasing dose of the water-soluble cellulose acetate. These results indicated that the water-soluble cellulose acetate with a low degree of substitution is useful as a lipid metabolism-improving agent and a prophylactic and/or therapeutic agent for diabetes.

EXAMPLE 9

A powdery high-fat diet was prepared by blending and mixing components including the water-soluble cellulose acetate prepared in Production Example 1 in the formulation given in Table 12.

REFERENTIAL EXAMPLE 8

The High Fat Diet 32 (CLEA Japan, Inc.) was used as a high-fat diet of Referential Example 8. The formulation of this feed can be found in Table 12.

TABLE 12

| Component | Example 9 Blending amount (weight percent) | Referential Example 8 Blending amount (weight percent) |
|---|---|---|
| Milk casein | 24.5 | 24.5 |
| Albumen powder | 5.0 | 5.0 |
| l-Cystine | 0.43 | 0.43 |
| Powdery beef tallow (containing 80% of beef tallow) | 15.88 | 15.88 |

TABLE 12-continued

| Component | Example 9 Blending amount (weight percent) | Referential Example 8 Blending amount (weight percent) |
|---|---|---|
| Safflower oil(oleic acid-rich type) | 20.0 | 20.0 |
| Crystalline cellulose | 5.5 | 5.5 |
| Water-soluble cellulose acetate | 2.0 | 0 |
| Maltodextrin | 8.25 | 8.25 |
| Lactose | 6.928 | 6.928 |
| Sucrose | 6.75 | 6.75 |
| AIN 93 vitamin mix | 1.4 | 1.4 |
| AIN 93 mineral mix | 5.0 | 5.0 |
| Choline bitartrate | 0.36 | 0.36 |
| tert-Butylhydroquinone | 0.002 | 0.002 |
| Total | 102.0 | 100.0 |

Evaluation Test 5: Therapeutic Effects on Non-Alcoholic Steatohepatitis

Suppressive/therapeutic effects of the water-soluble cellulose acetate on the onset of non-alcoholic steatohepatitis (hereinafter also referred to as NASH) were examined using STAM mice. The STAM mice offer pathogenesis, pathosis, and pathological progression extremely similar to those of human NASH.

The STAM mice were prepared according to the method of Stelic Institute & Co., Ltd. Specifically, female pregnant C57BL/6J mice (parous) (purchased from Charles River Laboratories Japan, Inc.) were fed with the AIN-93G standard diet (purified diet), while each mouse-bleeding cage housed one mouse. The formulation of the standard diet can be found in Table 1. Children were fed in the same cage with their mother until 3 weeks after delivery, and were fed as two mice per one cage from four weeks of age in early stages of the weanling stage. Infant mice corresponding to after-mentioned SHF and SHFW groups were treated with streptozotocin (STZ) two days after birth.

The child mice (male) were divided into two groups indicated in Table 13 from four weeks of age at the early stages of the weaning stage and fed with the AIN-93G standard diet or the high-fat diet of Referential Example 8 for one week, further divided into four groups indicated in Table 13 at the five weeks of age, where each group includes seven (7) mice. The mice belonging to the groups were further fed with the feeds given in Table 13.

TABLE 13

| | Feed | | Group name | n |
|---|---|---|---|---|
| Treatment | Four weeks of age | From five weeks of age | (abbreviation) | (number of mice) |
| Normal (without STZ treatment) | AIN-93G High-fat diet of Referential Example 8 (High Fat Diet 32) | AIN-93G High-fat diet of Referential Example 8 | NA group NHF group | 7 7 |
| STAM (with STZ treatment) | | High-fat diet High-fat diet of Example 9 | SHF group SHFW group | 7 7 |

The feeding environment was as follows. The temperature and humidity were those under a normal feeding environment, i.e., at a feeding temperature of 23° C.±2° C. and a humidity of 50%±10%, with a light-dark cycle with the light period of from 7 a.m. to 7 p.m. The mice had free access to feed and water (tap water).

The mice were fed with the feeds given in Table 13 to 8th week of age, while body weights were recorded throughout the feeding period. After the completion of feeding, the mice were fasted overnight, the abdomen was opened under Nembutal anesthesia, and the blood was collected from the posterior aorta using a syringe previously including 10 μL of EDTA. The amount of the collected blood was recorded so as to adjust the concentration after plasma separation. The mice were then dehematized, from which the liver was immediately excised and weighed. In addition, the spleen, adipose tissue, and cecum were extracted and weighed. From the cecum, the cecal contents alone were collected in a previously-weighed 2-mL tube and weighed.

The plasma was subjected to measurements of, as plasma biochemical analysis data, aspartate aminotransferase (AST), alanine aminotransferase (ALT), total cholesterol (TCHO), blood glucose level (GLU), total protein (TP), and albumin (ALB) using the FUJI DRI-CHEM (FUJIFILM Corporation).

Figure 16:
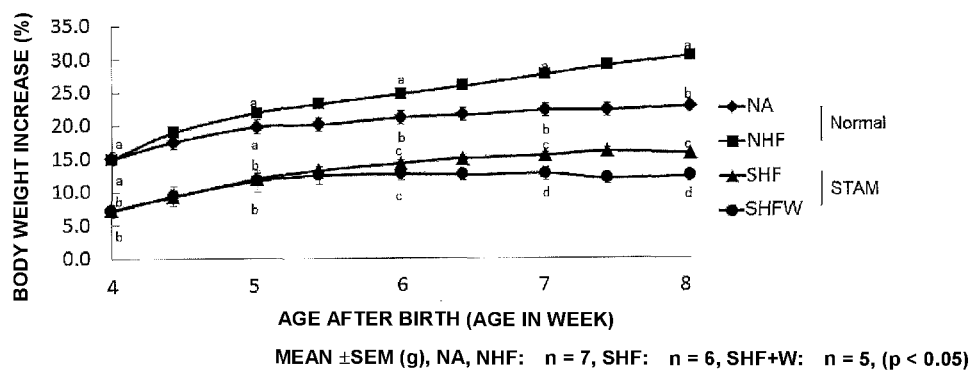
FIG. 16 is a graph illustrating the change in body weight increase of mice belonging to experimental groups (NA, NHF, SHF, and SHFW groups) in the evaluation test 5 in the experimental examples, where data with different letters of alphabet have a significant difference ($p<0.05$) from each other.
Figure 17:
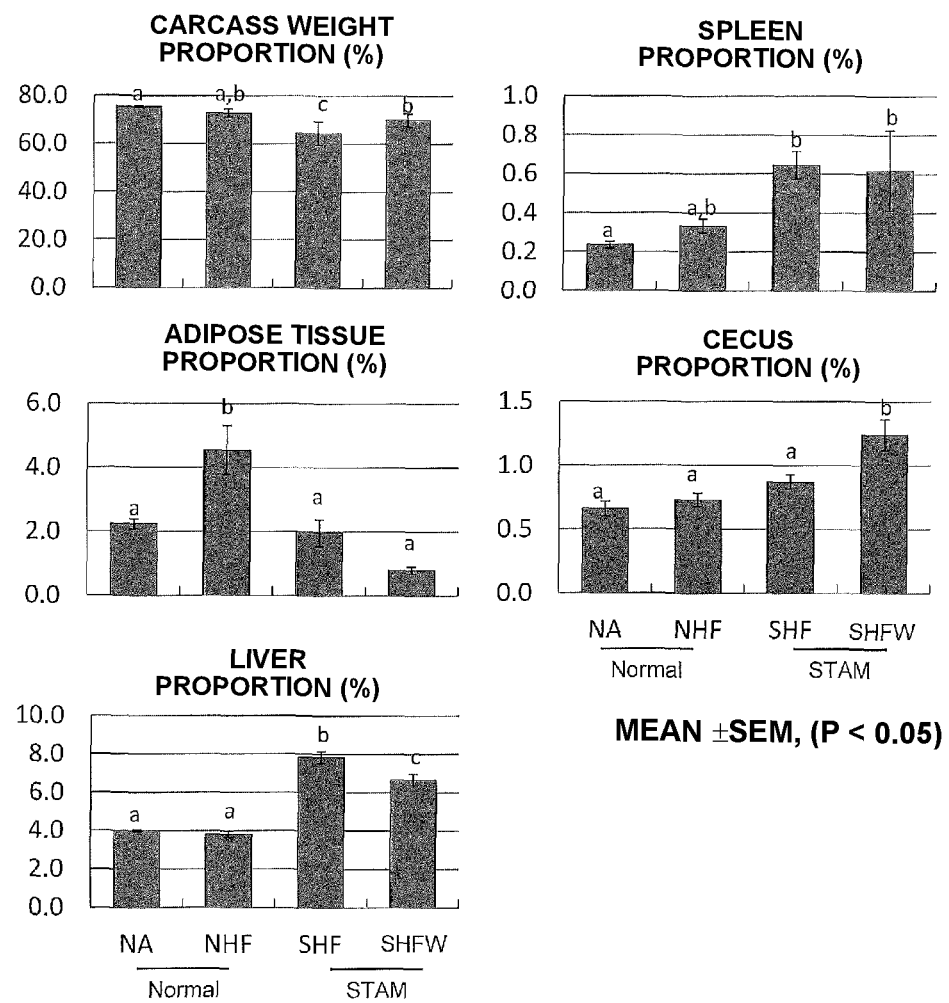
FIG. 17 depicts graphs illustrating proportions (%) of the carcass weight and organ weights, relative to the body weight upon dissection, of the mice belonging to the groups (NA, NHF, SHF, and SHFW groups) in the evaluation test 5 in the experimental examples, where data with different letters of alphabet have a significant difference (p<0.05) from each other.
Figure 18:
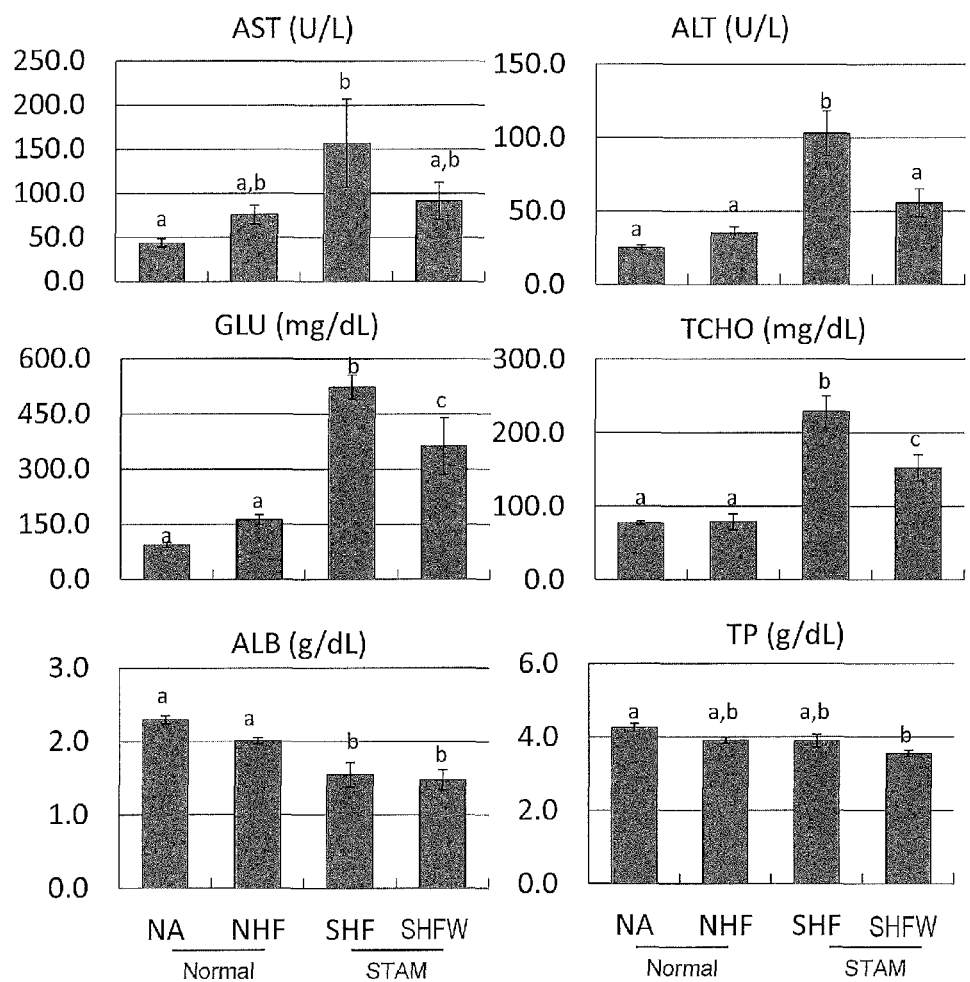
FIG. 18 depicts graphs illustrating plasma biochemical analysis data (AST, ALT, GLU, TCHO, ALB, and TP) of animals belonging to the groups (NA, NHF, SHF, and SHFW groups) in the evaluation test 5 in the experimental examples, where data with different letters of alphabet have a significant difference (p<0.05) from each other.

FIG. 16 is a graph illustrating the change in body weight increase; FIG. 17 depicts graphs illustrating proportions (%) of the carcass weight and organ weights, relative to the body weight upon dissection; Table 14 presents the plasma biochemical analysis data; and FIG. 18 depicts graphs illustrating graphed data of the plasma biochemical analyses.

TABLE 14

| | Normal | | STAM | |
|---|---|---|---|---|
| | NA | NHF | SHF | SHF + W |
| AST (U/L) | $44.1 \pm 4.8^a$ | $75.9 \pm 10.7^{a, b}$ | $157.2 \pm 49.9^b$ | $91.4 \pm 21.2^{a, b}$ |
| ALT (U/L) | $25.1 \pm 1.6^a$ | $35.1 \pm 4.1^a$ | $103.0 \pm 15.2^b$ | $55.8 \pm 9.5^a$ |
| TCHO (mg/dL) | $77.1 \pm 2.4^a$ | $78.7 \pm 10.8^a$ | $228.7 \pm 21.6^b$ | $152.2 \pm 17.7^c$ |
| TG (mg/dL) | $164.1 \pm 14.5$ | $86.9 \pm 11.6$ | $121.3 \pm 26.3$ | $131.2 \pm 38.8$ |
| GLU (mg/dL) | $93.7 \pm 7.1^a$ | $162.7 \pm 13.9^a$ | $523.2 \pm 33.0^b$ | $363.0 \pm 77.5^c$ |
| ALB (g/dL) | $2.3 \pm 0.1^a$ | $2.0 \pm 0.0^a$ | $1.6 \pm 0.2^b$ | $1.5 \pm 0.1^b$ |
| TP (g/dL) | $4.3 \pm 0.1^a$ | $3.9 \pm 0.1^{a, b}$ | $3.9 \pm 0.2^{a, b}$ | $3.6 \pm 0.1^b$ |

Mean ± SEM, (p < 0.05). Significantly different when indicated with different letters of alphabet.

FIG. 16 demonstrates that the SHF group and the SHFW group, each including the STAM mice, had been treated with STZ 2 days after birth, suffered from abnormal glucose tolerance (glucose intolerance), and had significantly lower body weights upon weaning as compared respectively with the NA group and the NHF group. The body weights at the final day had significant differences among all the groups.

FIG. 17 demonstrated that there was no significant difference in proportions of the carcass weight, the adipose tissue weight, and the spleen weight between the SHF group and the SHFW group; but the SHFW group had a significantly lower liver weight proportion and a significantly higher cecum weight proportion as compared with the SHF group. This indicated that the data are affected by the administration of the water-soluble cellulose acetate.

The SHF group had a significantly higher liver (weight) proportion as compared with the NHF group, and this demonstrated that the STAM mice suffer from hypertrophy of the liver. In contrast, the SHFW group had a significantly lower liver proportion as compared with the SHF group. This indicated that the water-soluble cellulose acetate, when administered, restrains hypertrophy of the liver, indicating that the administration of the water-soluble cellulose acetate may possibly improve, or restrain the onset of, the hepatic steatosis or NASH of the STAM mice.

Table 14 and FIG. 18 demonstrated that the SHFW group had AST and ALT at lower levels as compared with the SHF group, but had no significant difference in these data as compared with the NA and NHF groups. This indicated that the administration of the water-soluble cellulose acetate has improving effects on hepatic functions.

In addition, the SHF group had TCHO and GLU at significantly higher levels as compared with the Normal groups (NA and NHF groups), but the SHFW group had TCHO and GLU at significantly lower levels as compared with the SHF group, which levels more approximate to those of the Normal groups (NA and NHF groups). The result indicated that the water-soluble cellulose acetate, when administered, may possibly improve cholesterol metabolism disorders and abnormal glucose tolerance of the STAM mice.

Relating to nutritional conditions in the groups, there were significant differences in ALB and TP between the Normal groups (NA and NHF groups) and the STAM groups (SHF and SHFW groups). On the basis of these results and also in consideration of the body weight change, the STAM mice are assessed to be in low nutritional conditions. However, since there is no significant difference between the STAM groups (between the SHF group and the SHFW group), it was considered that the water-soluble cellulose acetate slightly affects the nutritional conditions.

INDUSTRIAL APPLICABILITY

The nutrient composition and the livestock feed according to the present invention have excellent effects of decreasing triglycerides. In addition, as compared with equivalents containing other water-soluble cellulose derivatives such as CMC, the nutrient composition and the livestock feed are highly safe. For example, they are intestine friendly and less cause diarrhea. The lipid metabolism-improving agent and the livestock-use lipid metabolism-improving agent according to the present invention have excellent lipid metabolism-improving action. The prophylactic and/or therapeutic agent for inflammatory bowel diseases and/or immune disorder according to the present invention is expected to offer excellent prophylactic and/or therapeutic effects on inflammatory bowel disease and/or immune disorder. The prophylactic and/or therapeutic agent for cancer according to the present invention has prophylactic and/or therapeutic effects on cancers (tumors). The prophylactic and/or therapeutic agent for obesity and/or diabetes according to the present invention has excellent prophylactic and/or therapeutic effects on obesity and/or diabetes. The prophylactic and/or therapeutic agent for non-alcoholic steatohepatitis according to the present invention has excellent prophylactic and/or therapeutic effects on non-alcoholic steatohepatitis. In addition and advantageously, the prophylactic and/or therapeutic agent for hypercholesterolemia according to the present invention has excellent prophylactic and/or therapeutic effects on hypercholesterolemia.

The invention claimed is:

1. A method for treatment of cancer in a subject in need thereof, comprising
administering to the subject an effective amount of a water-soluble dietary fiber selected from a cellulose acetate having a total degree of acetyl substitution of 0.4 to 1.1,
wherein the cellulose acetate comprises a cellulose acetate material having a compositional distribution index (CDI) of 2.0 or less, the compositional distribution index being specified by a formula:
CDI=(Measured value of half height width of chemical composition)/(Theoretical value of half height width of chemical composition) wherein:
the measured value of half height width of chemical composition is a half height width of chemical composition determined by high-performance liquid chromatographic (HPLC) analysis of a cellulose acetate propionate prepared by propionylating all residual hydroxy groups of the cellulose acetate material; and
the theoretical value of half height width of chemical composition is specified by a formula:

Theoretical value of half height width of chemical
    composition =2.35482
    $\sqrt{3*DPw*(DS/3)*(1-DS/3)}/DPw$    [Math. 1]

wherein:
DS is the total degree of acetyl substitution;
DPw is a weight-average degree of polymerization determined by a gel permeation chromatography-light scattering method using a cellulose acetate propionate prepared by propionylating all residual hydroxy groups of the cellulose acetate material.

2. The method according to claim 1,
wherein the subject is a livestock.

3. The method according to claim 1,
wherein the cancer is selected from the group consisting of liver cancer, colon cancer, mammary cancer, lung cancer, ovarian cancer, prostatic cancer, gastric cancer, and pancreatic cancer.

4. A method for treatment of non-alcoholic steatohepatitis in a subject in need thereof, comprising
administering to the subject an effective amount of a water-soluble dietary fiber selected from a cellulose acetate having a total degree of acetyl substitution of 0.4 to 1.1,
wherein the cellulose acetate comprises a cellulose acetate material having a compositional distribution index (CDI) of 2.0 or less, the compositional distribution index being specified by a formula:

CDI=(Measured value of half height width of chemi-
    cal composition)/(Theoretical value of half
    height width of chemical composition)

wherein:
the measured value of half height width of chemical composition is a half height width of chemical composition determined by high-performance liquid chromatographic (HPLC) analysis of a cellulose acetate propionate prepared by propionylating all residual hydroxy groups of the cellulose acetate material; and
the theoretical value of half height width of chemical composition is specified by a formula:

$$\text{Theoretical value of half height width of chemical composition} = 2.35482 \sqrt{3*DPw*(DS/3)*(1-DS/3)}/DPw \quad [\text{Math. 1}]$$

wherein:
DS is the total degree of acetyl substitution;
DPw is a weight-average degree of polymerization determined by a gel permeation chromatography-light scattering method using a cellulose acetate propionate prepared by propionylating all residual hydroxy groups of the cellulose acetate material.

5. The method according to claim 4, wherein the subject is a livestock.

6. A method for treatment of obesity and/or diabetes in a subject in need thereof, comprising
administering to the subject an effective amount of a water-soluble dietary fiber selected from a cellulose acetate having a total degree of acetyl substitution of 0.4 to 1.1,
wherein the cellulose acetate comprises a cellulose acetate material having a compositional distribution index (CDI) of 2.0 or less, the compositional distribution index being specified by a formula:

$$CDI = (\text{Measured value of half height width of chemical composition})/(\text{Theoretical value of half height width of chemical composition})$$

wherein:
the measured value of half height width of chemical composition is a half height width of chemical composition determined by high-performance liquid chromatographic (HPLC) analysis of a cellulose acetate propionate prepared by propionylating all residual hydroxy groups of the cellulose acetate material; and
the theoretical value of half height width of chemical composition is specified by a formula:

$$\text{Theoretical value of half height width of chemical composition} = 2.35482 \sqrt{3*DPw*(DS/3)*(1-DS/3)}/DPw \quad [\text{Math. 1}]$$

wherein:
DS is the total degree of acetyl substitution;
DPw is a weight-average degree of polymerization determined by a gel permeation chromatography-light scattering method using a cellulose acetate propionate prepared by propionylating all residual hydroxy groups of the cellulose acetate material.

7. The method according to claim 6, wherein the subject is a livestock.

8. A method for treatment of hypercholesterolemia in a subject in need thereof, comprising
administering to the subject an effective amount of a water-soluble dietary fiber selected from a cellulose acetate having a total degree of acetyl substitution of 0.4 to 1.1,
wherein the cellulose acetate comprises a cellulose acetate material having a compositional distribution index (CDI) of 2.0 or less, the compositional distribution index being specified by a formula:

$$CDI = (\text{Measured value of half height width of chemical composition})/(\text{Theoretical value of half height width of chemical composition})$$

wherein:
the measured value of half height width of chemical composition is a half height width of chemical composition determined by high-performance liquid chromatographic (HPLC) analysis of a cellulose acetate propionate prepared by propionylating all residual hydroxy groups of the cellulose acetate material; and
the theoretical value of half height width of chemical composition is specified by a formula:

$$\text{Theoretical value of half height width of chemical composition} = 2.35482 \sqrt{3*DPw*(DS/3)*(1-DS/3)}/DPw \quad [\text{Math. 1}]$$

wherein:
DS is the total degree of acetyl substitution;
DPw is a weight-average degree of polymerization determined by a gel permeation chromatography-light scattering method using a cellulose acetate propionate prepared by propionylating all residual hydroxy groups of the cellulose acetate material.

9. The method according to claim 8, wherein the subject is a livestock.

* * * * *